United States Patent [19]

Wright, Jr.

[11] Patent Number: 5,227,471
[45] Date of Patent: Jul. 13, 1993

[54] MONOCLONAL ANTIBODY PD41 THAT BINDS TO A PROSTATE MUCIN ANTIGEN THAT IS EXPRESSED IN HUMAN PROSTATIC CARCINOMA

[75] Inventor: George L. Wright, Jr., Norfolk, Va.

[73] Assignee: Eastern Virginia Medical School of the Medical College of Hampton Roads, Norfolk, Va.

[21] Appl. No.: 828,057

[22] Filed: Jan. 30, 1992

[51] Int. Cl.$^5$ .................. C12N 5/12; C12P 21/08
[52] U.S. Cl. ..................... 530/388.8; 530/388.15; 435/70.21; 435/172.2; 435/240.27
[58] Field of Search ............. 530/388.15, 388.8; 435/70.21, 172.2, 240.27

[56] References Cited

U.S. PATENT DOCUMENTS

| 4,671,958 | 6/1987 | Rodwell et al. | 424/85 |
|---|---|---|---|
| 4,741,900 | 5/1988 | Alverez et al. | 424/85 |
| 4,867,973 | 9/1989 | Goers et al. | 424/85.91 |
| 5,055,404 | 10/1991 | Ueda et al. | 435/240.27 |

OTHER PUBLICATIONS

Beckett, et al Cancer Research 51:1326–1333 1991.
Mazur, et al Am J. Clinical Pathology 93:466–470, 1990.
Wright et al., Prostate tumor-specific mucin-like antigen differentiates benign prostate hyperplasia from well-differentiated prostate adenocarcinoma, J. Urol., 145:259A, Abstract, 329, 1991.
Wright et al., Monoclonal antibody PD–41 identifies a marker specifically expressed on prostate carcinomas, J. Urol. 139:174A, Abstract 45, 1988.
Wright et al., TURP-27 and PD41; New markers for prostate cancer Proc. Amer. Assoc. Cancer Res. 29:249, Abst. 992. 1988.
Chu et al., Biochem Markers for Cancer, pp. 117–136, 1982.
Taga et al., Prostate 4:141–150, 1983.
Wang et al., Invest. Urol. 17:159–163, 1979.
Starling et al., Cancer Res. 46:367–374, 1986.
Horoszewicz et al., Anticancer Res. 7:929–936, 1987.
Kim et al., Cancer Res. 48:4543–4548, 1988.
Bazinet et al., Cancer Res. 48:6938–6942, 1988.
Wright et al., Radiopharm. 3:89, Abst. 193, 1990.
Frankel et al., Proc. Nat'l Acad. Sci. (USA) 79:903–907, 1982.
Raynor et al., J. Nat'l. Cancer Inst. 73:617–625, 1981.
Carroll et al. Clin. Immunol. Immunopath. 33:268–281, 1984.
Ware et al., Cancer Res. 42:1215–1222, 1982.
Kuroki et al., Int. J. Cancer 44:208–218, 1989.
Feller et al., Immunol. Series 53:631–672, 1990.
Mullinak et al., Proc. Nat'l. Acad. Sci. (USA) 87:8095–8099, 1990.
Starling et al., Cancer Res. 42:3084–3089, 1982.
Brothman et al., Int. J. Cancer 44:898–903, 1989.
Hoehn et al., Prostate 1:95–104, 1980.
Hoehn et al., Prostate 5:445–452, 1984.
Wright et al., Cancer Res. 43:5509–5516, 1983.
Wahab et al., Int. J. Cancer 36:677–683, 1985.
Kjeldsen et al., Cancer Res. 48:2214–2220, 1988.
Hakomori et al., Ann Rev. Immunol. 2:103–126 (1984).
Sell, Hum Pathol. 21(10):1003–1019, 1990.
Seregni et al., J. Nucl. Med. All. Sci. 34:314–320 (1990).
Lillehoj et al., Mol. Immunol. 19:1199–1202, 1982.
Nadji et al., Ann. NY Acad. Sci. 390:133–141, 1982.
Naritoku et al., J. Histochem. Cytochem. 30:253–260, 1982.
Papsidero et al., Hybridoma 2:139–147, 1983.
Frankel et al., Cancer Res. 42:3714–3718, 1982.
Wright et al., Int. J. Cancer 46:39–49, 1990.
Webb et al., Cancer Immunol. Immunother. 14:155–166, 1983.
Carroll et al., Surv. Synth. Path. Res. 3:189–200, 1984.
Raynor et al., Prostate 9:21–31, 1986.
Lingren et al., Cancer Immun. Immunother. 22:1–7, 1986.
Starling et al., Cancer Res. 45:804–808, 1985.
Kim et al., Cancer Res. 49:2379–2382, 1989.
Webb et al., Cancer Immunol. Immunother. 17:7–17, 1984.
Lopes et al., Cancer. Res. 50:6423–6429, 1990.
Arai et al., J. Immunol. 138:3259–3263, 1987.
Lipford et al., Cancer Res. 51:2296–2301, 1991.
Wright et al., Int. J. Cancer 47:717–725, 1991.
Wright et al., The Prostate 17:301–316, 1990.
Bazinet et al., J. Urol. 141:(Abs. 133), 1989.
Gallee et al., The Prostate 9:33–45, 1986.

*Primary Examiner*—David L. Lacey
*Assistant Examiner*—Donald E. Adams
*Attorney, Agent, or Firm*—Pennie & Edmonds

[57] ABSTRACT

Monoclonal antibodies that bind specifically to prostate carcinoma and do not bind substantially to normal prostate or benign prostatic hyperplasia, as well as hybridoma cell lines producing the monoclonal antibodies are disclosed. In one embodiment, a monoclonal antibody designated MAb PD41 is disclosed. A new antigen designated prostate mucin antigen is disclosed in isolated, substantially pure form. In addition, methods for using the hybridoma cell lines, the monoclonal antibody and/or the antigen for diagnosis, prophylaxis and/or treatment of prostate carcinoma are disclosed.

4 Claims, 9 Drawing Sheets

FIG. 3B

MONOCLONAL ANTIBODY PD41 THAT BINDS TO A PROSTATE MUCIN ANTIGEN THAT IS EXPRESSED IN HUMAN PROSTATIC CARCINOMA

TABLE OF CONTENTS

Field of the Invention
Background of the Invention
Summary of the Invention
    Abbreviations
Brief Description of the Figures
Detailed Description of the Invention
    Hybridoma Cell Line and Antibody Produced
    Characterization of MAb PD41 and PMA
    Applications
        Immunohistological and Immunocytological Applications
        Immunoserological Applications
        In Vivo Diagnostic, Prophylactic and Therapeutic Uses
        Other Uses
Examples
1. Preparation of Antibodies Specific for Prostate Carcinoma
2. Materials and Methods
    (2.1) Cell Lines
    (2.2) Tissues
    (2.3) Tumor Tissue Preparation
    (2.4) Immunoperoxidase Staining
    (2.5) Immunofluorescent Staining
    (2.6) Sodium Dodecyl Sulfate Polyacrylamide Gel Electrophoresis/Western Blotting Procedures
    (2.7) Competitive binding Assay
3. Results
    (3.1) Reactivity of MAb PD41 With Human Cell Lines and Blood Cells
    (3.2) Tissue Specificity of MAb PD41
4. Characterization of PMA Antigen

FIELD OF THE INVENTION

The invention relates to a novel monoclonal antibody that shows preferential binding to prostate carcinoma tissue with little or no cross-reactivity to benign prostatic hyperplasia or to normal prostate epithelium, as well as a hybridoma cell line and method for producing the antibody. Additionally, the present invention relates to a novel antigen with which the antibody reacts specifically.

BACKGROUND OF THE INVENTION

Several laboratories have developed monoclonal antibodies (MAbs) or immunoassays for monitoring the expression of the two well-characterized prostate antigens, i.e., prostatic acid phosphatase (PAP) (Chu et al., in T. M. Chu, ed., Biochemical Markers for Cancer, pp. 117-128, New York, Marcel Dekker, Inc., 1982; Taga et al., 1983, Prostate 4:141-150) and prostate-specific antigen (PSA) (Wang et al., 1979, Invest. Urol. 17:159-163). Neither of these prostate markers, however, has been found useful for early detection or for distinguishing benign from malignant prostate tumors. Moreover, these prostate markers do not provide meaningful information regarding the progressive nature or aggressiveness of the tumor.

Additional MAbs that have shown potential for detecting circulating prostate antigens in patient serum include TURP-27 (Starling et al., 1986, Cancer Res. 46:367-374), 7E11-C5 (Horoszewicz et al., 1987, Anticancer Res. 7:927-936) and PR92 (Kim et al., 1988, Cancer Res. 48:4543-4548). These antibodies recognize tumor antigens that are either prostate-organ specific, such that they react with normal and benign prostate antigens as well as carcinoma, i.e., PSA, PAP, 7E11-C5 and TURP-27, or they cross-react with non-prostate cells or carcinoma, i.e., PR92 cross-reacts with breast carcinomas.

U.S. Pat. No. 5,055,404 issued Oct. 8, 1991 to Ueda et al., describes monoclonal antibodies which recognize "differentiated antigen" specifically found on epithelial cells of human prostate including normal prostate, benign prostatic hyperplasia and prostatic cancer.

Two monoclonal antibodies described by Bazinet et al., (1988, Cancer Res. 48:6938-6942) recognize an antigen that is selectively expressed on malignant prostatic epithelium. However, these MAbs appear to identify only a small reactive subset of prostate carcinomas provided the tissue specimens have not been exposed to fixatives.

At present, there still remains a definite need for the identification of other prostate tumor associated antigens. In particular, there is a need for MAbs which preferentially bind to prostatic carcinoma and show little or no cross-reactivity to benign prostatic hyperplasia and normal prostatic epithelia. Such antibodies will be useful for both diagnosis and therapy of prostate carcinoma. Additionally, there is a need for MAbs specific for prostate carcinoma, that will be useful for early detection and monitoring of prostatic carcinoma disease and progression and/or which can provide additional clinical and pathological information with respect to aggressiveness or metastatic potential of prostate carcinoma.

SUMMARY OF THE INVENTION

The present invention encompasses hybridoma cell lines that produce novel monoclonal antibodies and the monoclonal antibodies (and fragments thereof) that show preferential specific binding to prostate carcinoma with little to no binding to benign prostatic hyperplasia or to normal prostate epithelium.

In a specific embodiment, the invention is directed to a hybridoma cell line PD41, having ATCC Accession No. HB 11094; and the PD41 monoclonal antibody produced by this cell line. The present invention further encompasses other monoclonal antibodies that bind to or recognize the PD41 antigen, designated the prostate mucin antigen (PMA), as well as monoclonal antibodies that competitively inhibit the binding of the PD41 monoclonal antibody produced by the hybridoma cell line ATCC Accession No. HB 11094 to PMA, as measured by an enzyme immunoassay, a radioimmunoassay or other competitive inhibition immunoassay.

The present invention additionally encompasses a novel antigen, PMA, in isolated or substantially pure form, to which the monoclonal antibodies of the invention bind, as well as methods and kits for using the antigen and/or the antibodies for detection or treatment or prophylaxis of prostate carcinoma.

The present invention also encompasses kits for using the monoclonal antibodies and/or antigen for in vitro or in vivo applications for diagnosis, monitoring, prophylaxis or therapy of prostate carcinoma.

In other embodiments, the invention encompasses compounds comprising the antigen binding region of the monoclonal antibodies of the invention or portions thereof, including Fv, F(ab')2, Fab fragments, chimeric antibodies, humanized antibodies, single chain antibodies, complementarity determining regions (CDRs), etc.

In yet other embodiments, the invention encompasses the use of the hybridoma cell lines as a source of DNA or mRNA encoding for the rearranged, activated immunoglobulin genes, which may be isolated, cloned by recombinant DNA techniques and transferred to other cells for the production of specific immunoglobulin specific for prostate carcinoma. By isolating rearranged DNA or preparing cDNA from the messenger RNA of the hybridoma cell line of the invention, a sequence free of introns may be obtained.

In still other embodiments, the invention encompasses the nucleotide sequence encoding the PMA antigen of this invention.

Abbreviations

The following abbreviations have the meanings indicated:

| | |
|---|---|
| MAb = | monoclonal antibody; |
| PAP = | prostatic acid phosphatase; |
| PSA = | prostate-specific antigen; |
| PMA = | prostate mucin antigen; |
| PBS = | phosphate-buffered saline (136 mM NaCl; 2.7 mM KCl; 8 mM Na$_2$HPO$_4$; 1.5 mM KH$_2$PO$_4$; 0.9 mM CaCl$_2$; 0.5 mM MgCl$_2$); |
| RIA = | radioimmunoassay |
| TBS = | Tris-buffered saline (20 mM Tris; 0.9% NaCl; 0.3% Tween 20; 5% bovine serum albumin); |
| BPH = | benign prostatic hyperplasia; |
| CDR = | complementarity determining region |
| CaP = | prostate adenocarcinoma; |
| NCA = | non-cross-reacting antigen; |
| TAA = | tumor-associated antigen; |
| TCC = | transitional cell carcinoma; and |
| BSM = | bovine submaxillary mucin. |

BRIEF DESCRIPTION OF THE FIGURES

FIGS. 3A–3B are representative Western immunoblot of normal, benign and carcinoma tissues. FIG. 3A is a blot of tissues or fluid samples reacted with MAb PD41: prostate carcinoma membrane extracts (Lanes 1, 2 and 3); CaP seminal plasma (Lane 4); membrane extracts from breast carcinoma (Lane 5); colon carcinoma (Lane 6); normal prostate (Lanes 7 and 8); BPH (Lanes 9 and 10); and normal seminal plasma (Lane 11), respectively. FIG. 3B is a blot as in FIG. 3A, but reacted with an isotype-matched negative control antibody. Blots were transferred from a 3–15% gradient SDS-PAGE gel (50 μg of protein loaded per Lane) onto immobilon-P transfer membrane and blotted. Blots were exposed to x-ray film for 72 hours. SG indicates top of separating gel. See text for details.

DETAILED DESCRIPTION OF THE INVENTION

Figure 1A:
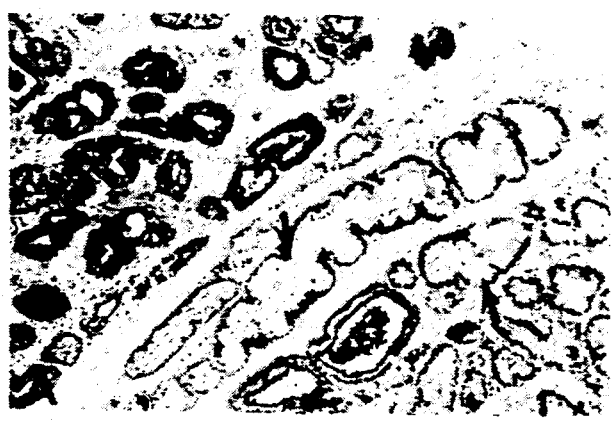
FIG. 1A, well- to moderately-differentiated prostate adenocarcinoma showing cytoplasmic staining of epithelial cells of neoplastic ducts as well as luminal secretions (upper left) and no staining of benign and normal ducts (arrows)×100.
Figure 1B:
FIG. 1B, well- to moderately-differentiated prostate adenocarcinoma showing intense staining of all tumor cells in a large cribriform neoplastic duct and little to no staining in smaller neoplastic ducts.×200 FIG. 1C, a large duct from a well differentiated prostate carcinoma with strong staining of epithelial cells and luminal contents.×400.
Figure 1C:
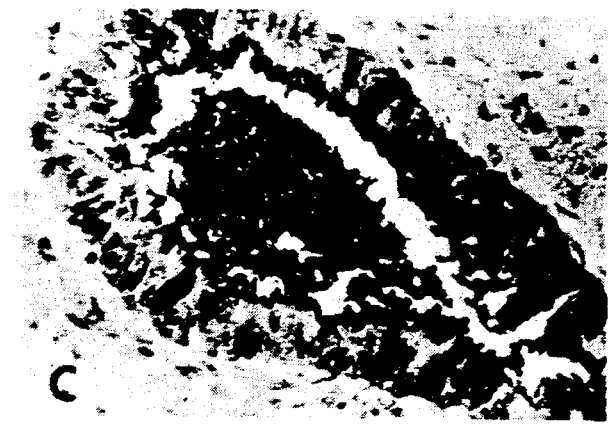
FIGS. 1(A–F) illustrates staining patterns of prostate carcinoma tissue sections with MAb PD41.
FIG. 1D, poorly differentiated prostate carcinoma with intense staining of tumor cells in most neoplastic ducts.×100 FIG. 1E, undifferentiated prostate carcinoma with very few tumor cells (arrows) staining.×200.
FIG. 1F, section from bone metastasis showing a large nest of intensely stained prostate tumor cells and no staining in cartilage and non-tumor tissue.×400.
Figure 1D:
Figure 1E:
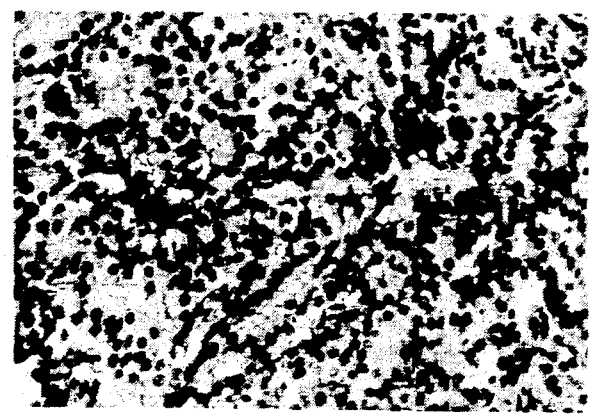

The present invention is directed to hybridoma cell lines, that produce monoclonal antibodies, and monoclonal antibodies specific for prostate carcinoma that are advantageously useful for detection, diagnosis and/or monitoring and for prophylaxis or treatment of pathological disease associated with prostate carcinoma. More particularly, the present invention encompasses a novel hybridoma cell line, which produces a monoclonal antibody that shows preferential binding to prostate carcinoma, with little or no specific binding to benign prostatic hyperplasia or to normal prostate epithelium. The invention further encompasses the monoclonal antibody specific for prostate carcinoma, which shows little or no binding to benign hyperplasia or normal prostate. The invention also encompasses other prostate carcinoma specific monoclonal antibodies that bind specifically with the novel antigen of the invention as well as antibodies that competitively inhibit binding of the antibody to the novel antigen of the invention.

In addition, the present invention is directed to a novel antigen, PMA, with which the monoclonal antibodies of the invention react, as well as methods and kits for using the antigen and/or antibodies for detection, prophylaxis or treatment of prostate carcinoma.

For ease of explanation, the description of the invention is divided into the following sections: (a) preparation of hybridoma cell lines and monoclonal antibodies; (b) characterization of the monoclonal antibodies and the novel antigen; and (c) applications for which the hybridoma cell lines, monoclonal antibodies and the antigen are suited.

Hybridoma Cell Line and Antibody Produced

In the embodiment of the present invention described in the Examples which follow, a crude membrane preparation of a moderately to poorly differentiated prostate adenocarcinoma was used as the "antigen" or immunogen. Based on results obtained and described in the Examples, the epitope recognized by the antibody of this invention is present in primary prostate carcinomas; including poorly-, moderately- and well-differentiated tumors; in metastatic prostate carcinomas; in seminal plasma; split ejaculates; and in prostatic fluids of prostate carcinoma patients as well as in a cultured colorectal carcinoma cell line LS180, dialyzed spent culture medium and the glycopeptide fraction digest of the LS180 cell line and in bovine submaxillary gland. Thus, such cells or fluids and/or membrane fractions or extracts thereof also represent potential "antigen" or sources of immunogen with which to immunize animals or cells to obtain somatic cells for fusion to generate antibodies of the invention.

Somatic cells with the potential for producing antibody and, in particular B lymphocytes, are suitable for fusion with a B-cell myeloma line. Those antibody-producing cells that are in the dividing plasmablast stage fuse preferentially. Somatic cells may be derived from the lymph nodes, spleens and peripheral blood of primed animals and the lymphatic cells of choice depend to a large extent on their empirical usefulness in the particular fusion system. Once-primed or hyperimmunized animals can be used as a source of antibody-producing lymphocytes. Mouse lymphocytes give a higher percentage of stable fusions with the mouse myeloma lines described below. Of these, the BALB/c mouse is preferred. However, the use of rat, rabbit, sheep and frog cells is also possible. As reviewed by Goding (in Monoclonal Antibodies: Principles and Practice, 2d ed., pp. 60–61, Orlando, Fla., Academic Press, 1986) use of rat lymphocytes may provide several advantages.

Alternatively, human somatic cells capable of producing antibody, specifically B lymphocytes, are suitable for fusion with myeloma cell lines. While B lymphocytes from biopsied spleens, tonsils or lymph nodes of individual may be used, the more easily accessible peripheral blood B lymphocytes are preferred. The lymphocytes may be derived from patients with diagnosed prostate carcinomas.

Myeloma cell lines suited for use in hybridoma-producing fusion procedures preferably are non-antibody-producing, have high fusion efficiency, and enzyme deficiencies that render then incapable of growing in certain selective media which support the growth of the desired hybridomas.

Several myeloma cell lines may be used for the production of fused cell hybrids of the invention, including P3-X63/Ag8, X63-Ag8.653, NS1/1.Ag 4 1, Sp210-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding in Monoclonal Antibodies: Principles and Practice, 2d ed., pp. 65–66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75–83, Amsterdam, Elseview, 1984).

Methods for generating hybrids of antibody-producing spleen or lymph node cells and myeloma cells usually comprise mixing somatic cells with myeloma cells in a 2:1 proportion as in the example below, (though the proportion may vary from about 20:1 to about 1:1), respectively, in the presence of an agent or agents (chemical or electrical) that promote the fusion of cell membranes. It is often preferred that the same species of animal serve as the source of the somatic and myeloma cells used in the fusion procedure. Fusion methods have been described by Kohler and Milstein [Nature 256:495–497 (1975) and Eur. J. Immunol. 6:511–519 (1976)], and by Gefter et al. [Somatic Cell Genet. 3:231–236 1977)]. The fusion-promotion agents used by those investigators were Sendai virus and polyethylene glycol (PEG), respectively. Fusion methods reviewed by Goding (in Monoclonal Antibodies: Principles and Practice, 2d ed., pp. 71–74, Orlando, Fla., Academic Press, 1986) including the above as well as electrically induced fusion are also suitable to generate monoclonal antibodies of the invention.

Fusion procedures usually produce viable hybrids at very low frequency, about $1\times10^{-6}$ to $1\times10^{-8}$ somatic cells Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells synthesize purine using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT media are hybrids formed from myeloma and spleen cells.

To facilitate screening of antibody secreted by the hybrids and to prevent individual hybrids from overgrowing others, the mixture of fused myeloma and B lymphocytes is diluted in HAT medium and cultured in multiple wells of microtiter plates. In two to three weeks, when hybrid clones become visible microscopically, the supernatant fluid of the individual wells containing hybrid clones is assayed for specific antibody. The assay must be sensitive, simple and rapid. Assay techniques include radioimmunoassays, enzyme immunoassays, cytotoxicity assays, plaque assays, dot immunobinding assays, and the like.

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels; the culture medium, also containing high concentrations of a single specific monoclonal antibody, can be harvested by decantation, filtration or centrifugation.

Characterization of MAb PD41 and PMA

Using techniques described generally in Section 5.1 and illustrated in the Examples, a new hybridoma cell line, PD41, that produces a novel MAb, PD41, that reacts selectively with prostate adenocarcinoma was generated. The present invention encompasses not only the PD41 MAb, but also, other monoclonal antibodies that bind specifically to PMA as well as any MAbs that competitively inhibit the binding of the PD41 MAb to PMA as assessed in an enzyme immunoassay, a radioimmunoassay or any other competitive binding immunoassay.

As demonstrated in the Examples which follow, the immunohistochemical reactivity of MAb PD41 is highly restricted to prostate carcinoma tissues, in particular ductal epithelia and secretions of prostate adenocarcinoma tissues. Sixty-five percent of the prostate tumor specimens examined stained with MAb PD41, whereas no staining of fetal or benign prostate specimens was observed. MAb PD41 reacts only minimally with normal prostate tissues, as less than of the epithelial cells of normal tissue specimens appear to stain, and then, only weakly. Moreover, MAb PD41 does not react with nonprostate carcinomas or a variety of normal non-prostate human tissues, although it is reactive with metastatic prostate carcinoma, e.g., in lymph nodes.

Additionally, preliminary experimental evidence demonstrates that MAb PD41 reacts with about 53% of prostatic intraepithelial neoplasia (PIN) lesions adjacent to PD41 positive staining tumor areas in primary prostate carcinoma. PIN is presently thought to be a precursor ("premalignant") to prostate carcinoma. Hence, PD41-positive reactivity in areas of PIN could be predictive of disease potential.

Also as demonstrated in the Examples, MAb PD41 does not react with available cultured human prostate tumor cell lines, including DU145, PC3, PC3-P, LNCaP and PPC-1, with human blood cells, or with purified antigens, including prostate-specific antigen (PSA) and prostatic acid phosphatase (PAP), using both radioimmunoassay and immunofluorescence procedures.

MAb PD41 binds specifically to target antigen present in seminal plasma obtained from prostate carcinoma patients, but not to seminal plasma from normal donors.

MAb PD41 can also be distinguished from other MAbs that bind specifically to prostate carcinoma, such as the recently described MAbs P25.48 and P25.91 (Bazinet et al., 1988, Cancer Res. 48:6438-6442). In contrast to MAb PD41 antigen, the P25 MAbs of Bazinet react with an antigen which is completely destroyed after chemical fixation of tissues and cannot be restored by enzymatic digestion. Further dissimilarity is evident on the basis of molecular weight of the respective antigens: P25.48 and P25.91 bind to a M, 58,000 protein (Bazinet et al., 1989, J. Urol. 141:203A), quite distinct from the antigen recognized by MAb PD41. Moreover, immunohistochemically the P25 MAbs do not react with well-differentiated CaPs as does PD41, but rather do react with a subpopulation of cells within higher grade tumors, i.e., poorly to undifferentiated tumors.

MAb PD41 also can be shown to be distinct from the anti-prostate MAbs PR92 (Kim et al., 1988, Cancer Res. 48:4543-4548) and 7E11-C5 (Horoszewicz et al., Anticancer Res. 7:927-936) on the basis of their respective antigens and cell-line reactivity. The PR92 antigen is reported to be a glycoprotein with an approximate molecular weight of 470,000 (unreduced) and 44,000 (reduced), whereas the antigen defined by 7E11-C5 consists of a single $M_r$ 100,000 band (reduced) (Wright et al., 1990, Radiopharm. 3:89, Abst. 193). PD41 also can be distinguished from the PR92 and 7E11-C5 MAbs, as well as several other prostate-directed MAbs, i.e., TURP-73 and TURP-27 (Starling et al., 1986, Cancer Res. 46:367-374), MAbs 35 and 24 (Frankel et al., 1982, Proc. Nat'l Acad. Sci. USA 79:903-907), KR-P8 (Raynor et al., 1981, J. Nat'l Cancer Inst. 73:617-625), the 3 F77 MAbs (Carroll et al., 1984, Clin. Immunol. Immunopathol. 33:268-281), and a-Pro-3 (Ware et al., 1982, Cancer Res. 42:1215-1222) on the basis of the reactivity of these MAbs to cultured cell lines and/or various normal, benign and neoplastic tissues.

As demonstrated in the Examples, the immunoblots of gel-separated components of prostate carcinoma tissue extracts indicate that the molecular weight of the proteins carrying the PD41 antigenic determinant differ among individual tumors, ranging from about $M_r$ 90,000 to greater than about 400,000. In seminal plasma from prostate carcinoma patients, the predominant component carrying the PD41 antigenic determinant is the diffuse $M_r > 400,000$ band.

The variability in molecular size of the PD41 antigen in prostate carcinoma extracts is similar to observations described from other carcinomas in which the reactive antigen is a high molecular weight glycoprotein or mucin-like tumor-associated antigen. (See Johnson et al., 1986, Cancer Res. 46:850-857; Lan et al., 1990, Cancer Res. 50:2993-3001; Burchell et al., 1983, J. Immunol. 131:508-513; Davis et al., 1986, Cancer Res. 46:6143-6148; Itkowitz et al., 1988, Cancer Res. 48:3834-3842; Kuroki et al., 1989, Int. J. Cancer 44:208-218; as well as a review article by Feller et al., 1990, Immunol. Series 53:631-672).

Data obtained in this study also suggest that the PMA antigen recognized by MAb PD41 is different from other mucin-like antigens identified on many non-prostate tumors. MAbs to these non-prostate mucins not only react with the tumor tissues or cell lines used for their generation, but also exhibit a spectrum of reactivity against other carcinomas and normal tissues. Preferential binding of PD41 to CaP and the virtual absence of reactivity with normal and non-prostate malignant tissues, particularly breast, colon, stomach, ovary, and pancreas, provide further evidence that MAb PD41 is distinct from other mucin-directed MAbs and that PMA is distinct from other mucin antigens. Additional support is provided by the inability of MAbs to other mucin-like TAAs to block PD41 binding to its target antigen. (See Section 6.4, below).

APPLICATIONS

Immunohistological and Immunocytological Applications

Monoclonal antibodies of the present invention can be used to detect potential prostate carcinoma cells in histological and cytological specimens, and, in particular, to distinguish malignant tumors from normal tissues and non-malignant tumors. For example, using the indirect immunoperoxidase assay described in Section 6.2.4, it has been observed that monoclonal antibodies of this invention stain (1) strongly to very strongly in well and moderately differentiated primary prostate carcinomas; (2) moderately to very strongly in poorly differentiated primary prostate carcinoma; and (3) moderately to strongly in undifferentiated primary prostate carcinomas. In addition, strong staining was observed in metastatic prostate carcinoma in lymph node, bone, breast and lung metastases. The PD41 MAb did not bind to fetal prostate tissues, frozen normal prostate tissues and fixed BPH tissues. One of 68 frozen BPH specimens and 3 of 22 fixed normal prostate specimens were PD41 positive; however, only weak staining was observed, in less than 1% of the ductal epithelial cells. With the exceptions noted above, no specific staining was observed in non-malignant prostate epithelial tissues nor in normal human organs and tissues examined.

As an alternative to immunoperoxidase staining, immunofluorescence techniques can use the monoclonal antibodies of the present invention to examine human specimens. In a typical protocol, slides containing cryostat sections of frozen, unfixed tissue biopsy samples or cytological smears are air dried, formalin or acetone fixed, and incubated with the monoclonal antibody preparation in a humidified chamber at room temperature.

The slides are then washed and further incubated with a preparation of antibody directed against the monoclonal antibody, usually some type of anti-mouse immunoglobulin if the monoclonal antibodies used are derived from the fusion of a mouse spleen lymphocyte and a mouse myeloma cell line. This antimouse immunoglobulin is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or exfoliated cells, i.e., single cell preparations from aspiration biopsies of prostate tumors using the monoclonal antibodies of the invention.

As shown in the Examples, preliminary evidence demonstrates that MAb PD41 reacts with about 53% of prostatic intraepithelial neoplasia (PIN) lesions adjacent to PD41 positive staining areas. PIN is presently thought to be a precursor of prostate carcinoma. Thus, in another embodiment of the invention, monoclonal antibodies of the invention can be used to examine PIN areas in histological and cytological specimens. Positive PD41 reactivity in such PIN areas may be useful to predict disease progression. By way of example, and not limitation, the monoclonal antibodies of the invention could be used in quantitation of the fluorescing tumor cells on tissue slides or exfoliated cells, i.e., single cell preparations from aspiration biopsies of prostate tumors by computer enhanced fluorescence image analyzer or with a flow cytometer. Use of MAb PD41 in such assays would be valuable to differentiate benign from malignant prostate tumors since the PMA antigen to which the monoclonal antibody binds is expressed only by malignant tumors. The percent PMA reactive cell population, alone or in conjunction with determination of the DNA ploidy of these cells, may, additionally, provide very useful prognostic information by providing an early indicator of disease progression. (See, Wright et al., 1990, Cancer 66:1242-1252, McGowan et al., 1990, Amer. J. Surg. 159:172-177).

In yet another alternative embodiment, the monoclonal antibodies of the present invention can be used in combination with other known prostate MAbs to provide additional information regarding the malignant phenotype of a prostate carcinoma. For example, the monoclonal antibody of the invention can be used in immunohistological or immunocytological tests as part of a panel of MAbs including such as the P25 MAbs of Bazinet et al. (supra) to distinguish early evidence of neoplastic change (PD41 MAb staining pattern) from potentially aggressive tumors (P25 MAb staining pattern).

IMMUNOSEROLOGICAL APPLICATIONS

The use of the monoclonal antibodies and/or the PD41 antigen described herein can be extended to the screening of human biological fluids for the presence of the specific antigenic determinant recognized. In vitro immunoserological evaluation of biological fluids withdrawn from patients thereby permits non-invasive diagnosis of cancers. By way of illustration, human fluids, such as prostatic fluid, seminal fluid, serum or urine can be taken from a patient and assayed for the specific epitope, either as released antigen or membrane-bound on cells in the sample fluid, using the anti-prostate carcinoma monoclonal antibodies in standard radioimmunoassays or enzyme-linked immunoassays known in the art, competitive binding enzyme-linked immunoassays, dot blot or Western blot, or other assays known in the art.

Kits containing the PD41 MAb or fragments of MAbs (as well as conjugates thereof) or PMA antigen of the invention can be prepared for in vitro diagnosis, prognosis and/or monitoring prostate carcinoma by the immunohistological, immunocytological and immunoserological methods described above. The components of the kits can be packaged either in aqueous medium or in lyophilized form. When the monoclonal antibodies (or fragments thereof) are used in the kits in the form of conjugates in which a label moiety is attached, such as a radioactive metal ion, the components of such conjugates can be supplied either in fully conjugated form, in the form of intermediates or as separate moieties to be conjugated by the user of the kit.

The kit may comprise one or more container means or series of container means such as test tubes, vials, flasks, bottles, syringes, or the like. A first of said container means or series of container means may contain the monoclonal antibody (or fragment thereof) or the PMA antigen of the invention. A second container means or series of container means may contain a label or linker-label intermediate capable of binding to the monoclonal (or fragment thereof) or PMA of the invention.

IN VIVO DIAGNOSTIC, PROPHYLACTIC AND THERAPEUTIC USES

The monoclonal antibodies or fragments thereof of this invention are particularly useful for targeting carcinoma cells in vivo. Thus, they can be used for tumor localization for detection and monitoring (enhancing patient management) as well as for therapy of primary prostate carcinoma and metastases. For these in vivo applications, it is preferable to use purified monoclonal antibodies or purified fragments of the monoclonal antibodies having at least a portion of an antigen binding region, including such as Fv, F(ab')2, Fab fragments, single chain antibodies, chimeric or humanized antibodies, CDRs, etc. Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2d ed., pp 104-126, Orlando, Fla., Academic Press).

For use in in vivo detection and/or monitoring of prostate carcinoma, the purified monoclonal antibodies can be covalently attached, either directly or via a linker, to a compound which serves as a reporter group to permit imaging of specific tissues or organs following administration and localization of the conjugates or complexes.

A variety of different types of substances can serve as the reporter group, including such as radiopaque dyes, radioactive metal and non-metal isotopes, fluorogenic compounds, fluorescent compounds, positron emitting isotopes, non-paramagnetic metals, etc.

For use in in vivo therapy of prostate carcinoma, the purified monoclonal antibodies can be covalently attached, either directly or via a linker, to a compound which serves as a therapeutic agent to kill and/or prevent proliferation of the malignant cells or tissues following administration and localization of the conjugates. A variety of different types of substances can serve as the therapeutic agent including radioactive metal and non-metal isotopes, chemotherapeutic drugs, toxins, etc.

Methods for preparation of antibody conjugates of the antibodies (or fragments thereof) of the invention useful for detection, monitoring and/or therapy are described in U.S. Pat. Nos. 4,671,958; 4,741,900 and 4,867,973.

Kits for use with such in vivo tumor localization and therapy methods containing the monoclonal antibodies (or fragments thereof) conjugated to any of the above types of substances can be prepared. The components of the kits can be packaged either in aqueous medium or in lyophilized form. When the monoclonal antibodies (or fragments thereof) are used in the kits in the form of conjugates in which a label or a therapeutic moiety is attached, such as a radioactive metal ion or a therapeutic drug moiety the components of such conjugates can be supplied either in fully conjugated form, in the form of intermediates or as separate moieties to be conjugated by the user of the kit.

Other components of the kits can include such as those mentioned in Section 5.3.2 above.

OTHER USES

The PMA antigen of the present invention is a unique antigen selectively expressed by prostate carcinomas. It is envisaged that PMA and the PD41 MAb will additionally be valuable to study the natural history, development, effect of hormone/drug manipulation, etc. of prostate carcinoma.

In another embodiment of the invention, the PMA may be used to prepare a vaccine formulation for prostate carcinoma. Either purified native PMA (see, Kaufman et al., 1991, Int. J. Can. 48:900-907) or the nucleotide sequence encoding PMA inserted into a virus vector such as vaccinia virus (see. Moss., 1991, Sci. 252:1662-1667) can serve as the immunogen for the vaccine formulation of this embodiment.

In other embodiments, the hybridoma cell lines, including, in particular, the PD41 hybridoma cell line, of the present invention may be used to produce compositions comprising an antigen binding site or antibody variants which combine the murine variable or hypervariable regions with the human constant region or constant and variable framework regions, i.e., chimeric or humanized antibodies as well as humanized antibodies that retain only the antigen-binding CDRs from the parent PD41 MAb in association with human framework regions (see, Waldmann, 1991, Sci. 252:1657, 1662, particularly 1658-59 and references cited therein). Such chimeric or humanized antibodies retaining binding specificity of the antibodies of the invention would be expected to have reduced immunogenicity when administered in vivo for diagnostic, prophylactic or therapeutic applications according to the invention.

In yet other embodiments, the invention encompasses the use of the hybridoma cell lines as a source of DNA or mRNA encoding for the rearranged, activated immunoglobulin genes, which may be isolated, cloned by known recombinant DNA techniques and transferred to other cells for the production of antigen binding fragments specific for prostate carcinoma. By isolating rearranged DNA or preparing cDNA from the messenger RNA of the hybridoma cell line of the invention, a sequence free of introns may be obtained.

To illustrate, and not by way of limitation, an immunoexpression library can be prepared and screened for antibody binding fragments for PMA as follows (See. Huse et al., 1989, Sci. 246:1275-1281; Mullinax et al., 1990, Proc. Nat'l Acad. Sci. USA 87:8045-8099). Total RNA can be purified (e.g., using commercially available kits) and converted to cDNA using an oligo (dT) primer for the light (L) chain and a specific primer for the heavy (H) chain using reverse transcriptase. Polymerase chain reaction (PCR) amplification of the immunoglobulin H and L chain sequences can be done separately with sets of primer pairs. Upstream primers can be designed to hybridize to partially conserved sequences in the leader and/or framework regions of $V_H$ or $V_L$ and downstream primers can be designed to hybridize to constant domain sequences. Such primers would preserve full length L chain and provide H chains corresponding to the Fd of IgG and conserving the H-L disulfide bonds. The PCR amplified L and H DNA fragments are then digested and separately ligated into H and L chain vectors. Such vectors contain a pelB leader sequence, a ribosome binding site and stop codons. Suitable λ phage vectors for expression in E. coli can be prepared from commercially available vectors (ImmunoZAP L, ImmunoZAP H; Stratacyte, La Jolla, Calif.). The ligated recombinant phage DNA is incorporated into bacteriophage with in vitro packaging extract and used to infect *E. coli*. The immunoexpression library thus created is screened for antigen binding fragments using PMA. Positive clones can be screened and identified as described by Mullinax et al. (supra).

In still other embodiments, the invention encompasses the nucleotide sequence encoding the PMA antigen of this invention. The PMA antigen of the invention may be isolated and purified using only methods known in the art based on binding to the PD41 MAb of the present invention. For example, and not by way of limitation, PMA may be isolated from extracts of prostate carcinoma either by affinity chromatography, in which the PD41 MAb is bound to a solid support, or by preparative SDS-polyacrylamide gel electrophoresis, in which gel slices containing PMA are identified by allowing labeled PD41 MAb to bind to the antigen. The PMA may require further purification and is subjected to amino acid sequencing using known techniques. Oligonucleotide probes corresponding to the amino acid sequence thus obtained may be generated by standard techniques and then used to identify DNA or genomic clones encoding PMA using standard techniques including PCR (see generally, Sambrook et al., in Molecular Cloning: A Laboratory Manual, 2d. ed., Cold Spring Harbor Laboratory Press, 1989). Once the gene encoding PMA is cloned, it can be produced in large quantity using standard expression systems. Alternatively, the PMA gene can be cloned by a "shotgun" approach in which genomic DNA or, preferably, cDNA obtained from prostate carcinoma cells may be used to create an expression library in which clones expressing PMA are identified by binding to labelled PD41 MAb using standard techniques.

The following examples are intended as non-limiting illustrative examples of certain embodiments of the present invention.

EXAMPLES

Some of the results described below are described in Beckett et al., 1991, Cancer Res. 51:1326-1333.

1. PREPARATION OF ANTIBODIES SPECIFIC FOR PROSTATE CARCONOMA

Production of MAbs. Three female BALB/c mice (8 weeks old; Harlan Sprague-Dawley, Indianapolis, Ind.) were hyperimmunized in at monthly intervals with 100 µg of a crude membrane preparation from a moderately to poorly differentiated prostate adenocarcinoma surgical specimen mixed 1:1 with Freunds Complete Adjuvant (FCA), initial injection, or Freunds Incomplete Adjuvant (FICA), subsequent 2 monthly injections. Following a final iv injection of the membrane preparation alone, immunized spleen cells were harvested and fused at a 2:1 ratio with NS1/1.Ag4.1 mouse myeloma cells in the presence of 50% PEG. Hybridoma production was performed as described previously. (Starling et al., 1986, Cancer Res. 46:367-374).

Screening of Hybridoma Supernatants. Supernatants from actively growing hybridomas were screened for reactivity against the immunizing material and for negative reactivity against PSA and PAP antigens and a panel of normal cells (AB+ and O RBC, WBC, and fibroblasts) by a solid-phase RIA. (Starling et al., 1982, Cancer Res. 42:3084-3089) One hybrid, designated PD41.84 (PD41), was selected for further analysis, sub-cloned using a Coulter Epics 5 flow cytometer, and isotyped (IgGl,k) using an enzyme-linked immunosorbent assay and kit (Hyclone Laboratories, Logan, Utah).

Thus, following the procedure of the invention, hybridoma cell line PD41 was obtained. The hybridoma cell line was cultured to produce monoclonal antibody PD41 in sufficient quantity for characterization and further analysis as described below.

2. MATERIALS AND METHODS

2.1 Cell Lines

Human tumor cell lines were grown in nutrient medium supplemented with serum additives as recommended by the supplier of the line. The source of many cell lines used in this study has been described in earlier publications. (Starling, et al., 1986, Cancer Res. 46:367-374; Starling et al., 1982, Cancer Res. 42:3084-3089). The cell lines evaluated, include the following: T24, CUB1, SW733, 253J, SCaber, J82, RT4, EJ, TCCSUP, SW780, HT1376, CUB3, and HU609 (bladder); DU145, PC3, PC3-P, LNCaP, and PPC-1 (Brothman et al., 1989, Int. J. Cancer 44:898-903) (prostate); Calu-1, A-427, Plano-1, SKLU-1, A549, SKMES-1, OH-1, and SKLC-2 (lung); VAMT-1, JMN, and NCI28 (mesothelioma); MCF-7, SKBr3, and ZR-75-1 (breast); LS174, CX-1, SW480, SW1463, and LS180 (colorectal); A375, WM56, and H1477 (melanoma); PANC-1 and MIA (pancreatic); CMVMJHEL-1 (cytomegalovirus transformed fibroblast); and CCRF-HSB2 (human T-cell lymphocytic leukemia).

2.2 Tissues

Fresh surgical or autopsy specimens as well as formalin-fixed, paraffin-embedded blocks of various human tissues were obtained from the Department of Pathology of Sentara Norfolk General Hospital, Norfolk, Va.; the Department of Pathology of the Veterans Administration Hospital, Hampton, VA; the Cooperative Human tissue Network, University of Alabama at Birmingham; and the National Disease Research Interchange, Philadelphia, Pa.. Tissues for paraffin blocks were fixed in neutral buffered 10% formalin, whereas those for frozen sections were embedded in Tissue-Tek OCT Compound (10.24% w/w polyvinyl alcohol, 4.26% w/w carbowax, and 85.50% w/w non-reactive ingredients) and snap-frozen in isopentane over liquid nitrogen. Paraffin blocks of various passages of the prostatic carcinoma xenografts PC-82, PC-EW, and PC-EG were kindly provided by Dr. Gert Jan Van Steenbrugge, University of Rotterdam, and Dr. Zoltan Csapo, Department of Urology, Zentralklinikum, Augsburg, Federal Republic of Germany. The origin and establishment of these xenografts have been described previously. (Hoehn, et al., 1980, Prostate 1:95-104; in G.B.A Bastert et al., eds., Thymus Aplastic Nude Mice and Rats in Clinical Oncology, pp. 413-415, Stuttgart, N.Y., Gustav Fischer Verlag, 1981; and 1984, Prostate 5:445-452).

2.3 Tumor Tissue Preparation

Crude membrane preparations were prepared from prostate carcinoma specimens or other tissues by first finely mincing the tissue in 10 ml of 1.0 mM NaHCO$_3$ buffer containing 200 µl of a 50× protease cocktail (antipain, 3.4 mg; pepstatin, 10.0 mg; EDTA, 0.372 g (Sigma Chemical Co., St. Louis, Mo.) dissolved in 20.0 ml of DDH$_2$O). The minced tumor tissue was then homogenized in a Polytron (Brinkman Instruments, Westbury, N.Y.) and further disrupted using Wheaton glass homogenizers. The homogenate was centrifuged at 2000× g for 5 min, and the supernatant resulting from this spin was further centrifuged (2 h, 138,000× g, 4° C.). The resulting pellet was resuspended in a minimum volume of PBS and stored at −70° C. Protein concentrations were determined using the Bicinchoninic Acid (BCA) Protein Assay (Pierce Chemical Co., Rockford, Ill.).

2.4 Immunoperoxidase Staining

The staining reactivity on frozen or fixed tissues was evaluated by the avidin-biotin peroxidase assay using the ABC Elite Vectastain kit (Vector Laboratories, Burlingame, Calif.) as described previously. (Wright et al., 1983, Cancer Res. 43:5509-5516; Wahab et al., 1985, Int. J. Cancer 36:677-683). Following development with the chromogen 3,3'-diaminobenzidine tetrahydrochloride (Sigma), the tissues were counterstained with Mayer's hematoxylin and mounted in aquamount (Learner Laboratories, Pittsburgh, Pa.). Tissues were scored independently by 2 investigators for both intensity of reactivity, using a scale of 0 (absence of staining) to 4+ (most intense staining) as well as for numbers of cells positive in each specimen.

2.5 Immunofluorescent Staining

Cells for immunofluorescence analysis were removed from culture flasks either by scraping or with PBS-EDTA; PBS-washed cells were pelleted for use in either live-cell or fixed-cell (25% ethanol, on ice, 15 min) indirect immunofluorescence. MAb PD41 culture supernatant (100 µl) was added to test wells and incubated at 4° C. for 60 min. After the cells were washed in PBS, they were incubated for 30 min at 4° C. with 50 µl of fluorescein-conjugated goat anti-mouse IgGs (Organon Teknika-Cappel, Malvern, Pa.) at 50 µg/ml. The cells were again washed and observed for fluorescent staining using an Olympus microscope equipped with a fluorescence vertical illuminator system. The percent of intact cells showing fluorescence and their staining intensity (scale 0 to +4), out of a total of 300 cells analyzed, was determined.

2.6 Sodium Dodecyl Sulfate-Polyacrylamide Gel Electrophoresis/Western Blotting Procedures Electrophoresis was carried out in polyacrylamide gels under reducing conditions [Laemmli et al., 1970, Nature (London) 227:680-685], and protein migration in gels was determined using Rainbow protein molecular weight markers (Amersham, Arlington Heights, Ill.). Proteins separated by electrophoresis were transferred to an immobilon-P transfer membrane (Millipore, Bedford, Mass.) at 25 V for 12 h (Tobin et al., 1979, Proc. Nat'l Acad. Sci. USA 76:4350-4354) using transfer buffer without methanol. Following transfer of the proteins, the membrane was placed in TBS blocking buffer (1 h at 37° C.). The membrane was incubated with PD41 MAb culture supernatant (20 µg/ml, 2 h, 25° C.) or an isotype matched control antibody. Membranes were washed in dilute TBS to remove unbound antibody, then incubated with $^{125}$I-labeled rabbit anti-mouse IgG (secondary antibody, specific activity 1.25 µCi/µg) at 1×10$^7$ cpm/50 ml of TBS for an additional 2 h at 25° C. Following incubation with the secondary antibody, the membrane was further washed, air dried, and exposed to Kodak XAR X-ray film (−70° C., 48-72 h). The membranes were gently agitated during all incubations.

2.7 Competitive Binding Assay

Purified PD41 MAb was labeled with $^{125}$I-labeled sodium iodide (specific activity, 1.25 µCi/µg) by the conventional chloramine-T method. Unbound iodine was removed from the $^{125}$I-labeled MAb product by a membrane ultrafiltration technique established in our laboratory (Lipford et al., 1990, Anal. Biochem. 187:133-135). Twenty-five µl of unlabeled antibody (blocking antibody) at varying concentrations from 0 to 100 µg/ml were incubated with the antigen-coated wells (3 µg/well) for 2 h at 25° C. After a series of washes, 25 µl of $^{125}$I-labeled PD41 MAb were added at approximately 50% binding activity and incubated an additional 2 h. Following additional wash steps, the wells were dried and cut, and the radioactivity remaining in the wells was determined. The blocking antibodies used were MAb B72.3 (a gift from Dr. Jeffrey Schlom, Laboratory of Tumor Immunology and Biology, National Cancer Institute Bethesda, Md. see U.S. Pat. No. 4,522,918), anti-carcinoembryonic antigen (CEA) MAb (Zymed, San Francisco, Calif.) that had been adsorbed to eliminate reactivity to non-cross-reacting antigen, and anti-HMFG-2 MAb (Unipath Limited, Bedford, United Kingdom).

3. RESULTS

3.1 Reactivity of MAb PD41 With Human Cell Lines and Blood Cells

Monoclonal antibody PD41 was screened against a panel of 44 cultured human tumor cell lines (see Section 1. above) and normal human blood cells using both fixed-cell indirect radioimmunoassay (RIA) and live and fixed-cell indirect immunofluorescence. Results are shown in Table 1.

TABLE 1

Reactivity of MAb PD41 to Malignant Cell Lines and Human Blood Cells by Indirect RIA and Indirect Immunofluorescence

| | No. Positive/No. Tested | | |
|---|---|---|---|
| Target cell | RIA[a] | Immunofluorescence[b] | Immunofluorescence[c] |
| TCC (bladder) | 0/12 | 0/3 | 0/3 |
| Prostate | 0/4 | 0/5 | 0/5 |
| Breast | 0/1 | 0/3 | 0/3 |
| Lung | 0/10 | 0/4 | 0/4 |
| Adenocarcinoma | 0/6 | 0/3 | 0/4 |
| Small cell | 0/1 | 0/1 | 0/1 |
| Mesothelioma | 0/3 | NT[d] | NT |
| Colorectal | 0/3 | 1/5[e] | 0/3 |
| Pancreatic | 0/2 | NT | NT |
| Melanoma | NT | 0/3 | 0/3 |
| Blood cells | | | |
| RBC (AB+/−) | 0/3 | 0/3 | 0/3 |
| WBC | 0/4 | 0/4 | 0/4 |

[a]Values given are for a fixed-cell radioimmunoassay as described in Section 2.
[b], [c]Values given are for a live-cell (b) and a fixed-cell (c) indirect immunofluorescence assay as described in Section 2.
[d]NT = not tested.
[e]Reactivity to LS180, a colorectal carcinoma.

As demonstrated in Table 1, only one cultured tumor cell line, LS180, a colorectal carcinoma, reacted with the PD41 MAb. PD41 reactivity was also detected in the concentrated, dialyzed spent culture medium and the glycopeptide fraction digest from the LS180 cell line (data not shown). No other cell type, including the 5 prostate cell lines, i.e., DU145, PC3, PC3-P, LNCaP, and PPC-1, expressed the PD41 antigen.

3.2 Tissue Specificity of MAb PD41

The tissue specificity of monoclonal antibody PD41 was determined using an avidin biotin complex immunoperoxidase assay (see Section 2.4 above). The results are presented in Table 2 and FIGS. 1 (A–F) and 2.

TABLE 2

Reactivity of Monoclonal Antibody PD41 to Formalin-Fixed or Frozen Prostate Tissues by Indirect Immunoperoxidase Assay

| Tissue Type | No. Positive/No. Tested (% Positive) Frozen | No. Positive/No. Tested (% Positive) Fixed | Staining intensity[a] | % Positive Cells[b] |
|---|---|---|---|---|
| Primary Carcinoma | 52/65 (80) | 43/81 (53) | 3–4+ | 2–95 |
| WD[c] | 14/15 (93) | 12/20 (60) | 3–4+ | 3–90 |
| MD | 13/15 (87) | 9/12 (75) | 3–4+ | 3–95 |
| PD | 24/29 (83) | 20/25 (80) | 2–4+ | 2–95 |
| UD | 1/6 (17) | 2/24 (8) | 2–3+ | 2–10 |
| Metastatic to: | | | | |
| Bladder | 0/1 (0) | 0/2 (0) | 0 | 0 |
| Bone | 0/1 (0) | 1/2 (50) | 3–4+ | 80–90 |
| Breast | 1/1 (100) | 1/2 (50) | 2+ | <1 |
| Liver | NT[d] | 0/3 (0) | 0 | 0 |
| Lung | NT | 1/3 (33) | 3+ | 30–40 |
| Lymph node | NT | 0/1 (0) | 0 | 0 |
| BPH | 1/68 (1) | 0/48 (0) | 1–2+ | <1 |
| Normal | 0/18 (0) | 3/22 (14) | 1–3+ | <1 |
| Fetal[e] | 0/3 (0) | 0/5 (0) | 0 | 0 |
| Nude Mouse Xenografts | | | | |
| PC-82 | NA[d] | 1/2 (50) | 2+ | 2 |
| PC-EW | NA | 1/2 (50) | 3–4+ | 23 |
| PC-EG | NA | 0/2 (0) | 0 | 0 |

[a]Staining intensity: 0 = no staining. 1+ = weak staining, 2+ = moderate staining, 3+ = strong staining, and 4+ = very strong staining.
[b]Intensity and percent positive cells apply to both fixed or frozen tissues.
[c]WD, MD, PD, UD: well, moderately, poorly, and undifferentiated prostate carcinoma.
[d]NT, NA: not tested, not available.
[e]Fetal tissue obtained from second and third trimester specimens.

As demonstrated in Table 2, PD41 MAb reacts to both frozen and fixed primary prostate carcinoma. Considering only those cases in which 10% or more of the tumor cells are identified by PD41, the sensitivity for prostate cancer specimens is 47% (fixed tissues) and 65% (frozen tissues). In instances in which both fixed and frozen specimens from the same case could be evaluated, 26% of the fixed specimens failed to stain, suggesting the possibility that some denaturation of the target antigen may occur during either the formalin fixation or deparaffinization procedures. In either case, strong staining of the tumor cells was observed in the majority of the PD41-positive prostate carcinoma specimens (FIG. 1). The PD41 staining appears confined to an antigen expressed by prostatic epithelial cells, although staining of luminal secretions and the borders of the ductal epithelial cells was also observed (FIG. 1). The staining pattern was, however, very heterogeneous with the number of PD41-positive tumor cells ranging from 2 to 95% (Table 2) irrespective of specimen preparation (FIG. 2), and this pattern of expression remained fairly constant for the differentiated carcinomas (i.e. well, moderately, and poorly differentiated) (Table 2; FIG. 2). Undifferentiated primary prostate carcinomas (those with no glandular elements present), on the other hand, appeared to lack PD41 expression (FIG. 1E; FIG. 2).

Figure 1F:
Figure 2:
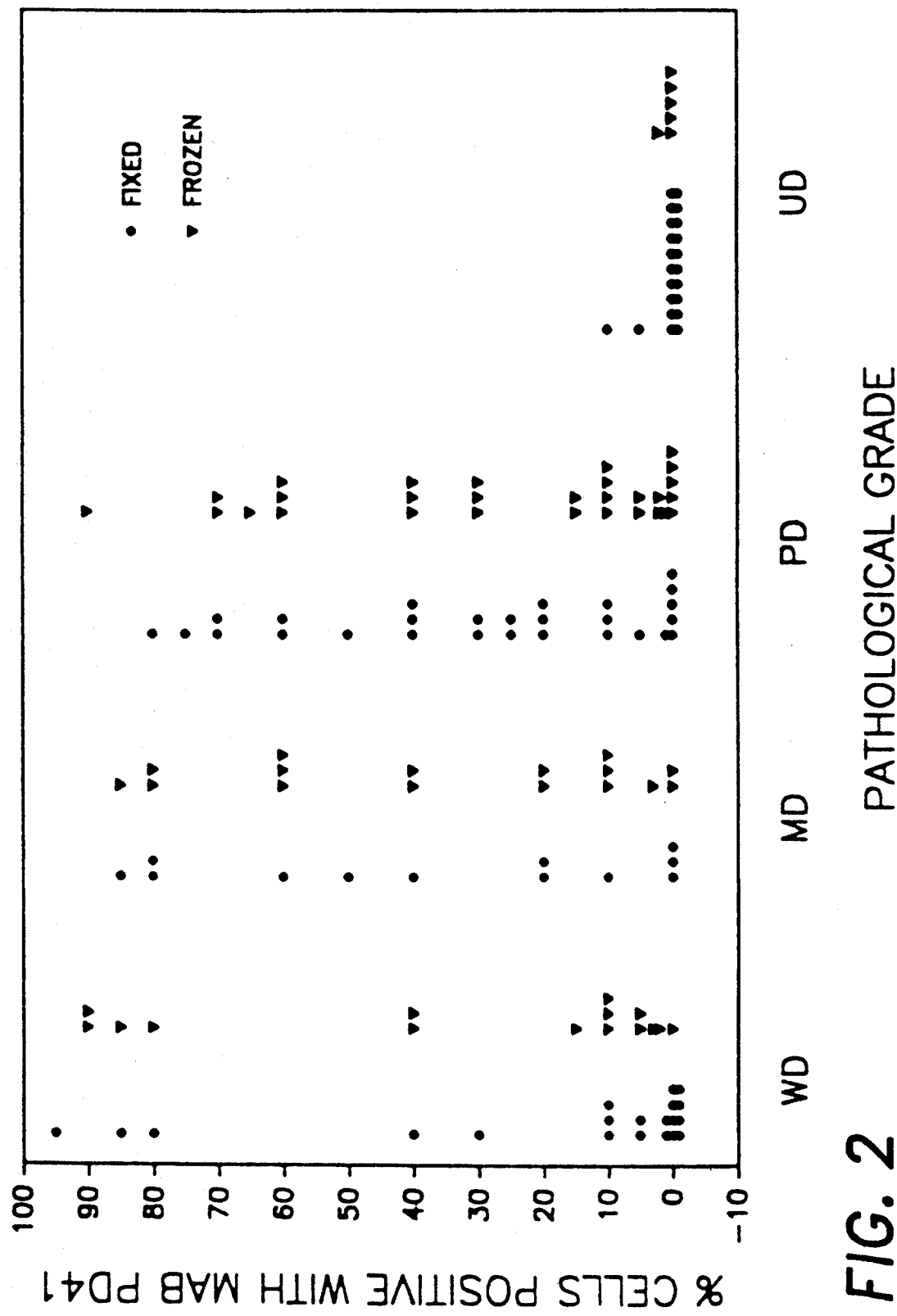
FIG. 2 is a scattergram representing the percentage of cells staining with PD41 MAb in fixed or frozen well differentiated (WD), moderately differentiated (MD), poorly differentiated (PD), and undifferentiated (UD) prostate carcinomas. Symbols indicate, percent of positive cells in a given tumor sample.

PD41 antigen detection was observed in bone, breast, and lung metastases tested (Table 2), with intense staining in the majority of the tumor cells of one metastatic bone specimen (FIG. 1F).

PD41 MAb did not bind substantially to fetal prostate tissues, frozen normal prostate tissues, and fixed BPH tissues (Table 2). One of 68 frozen BPH specimens and 3 of 22 fixed normal prostate specimens were PD41-positive, however only weak staining was observed in less than 1% of the ductal epithelial cells.

The PD41 target antigen also was expressed in the tumor cells of 2 nude mouse prostate xenografts (Table 2), and the staining pattern observed, especially in the PC-EW heterotransplant, was similar to that described above for human prostate surgical specimens.

Both the number and intensity of the stained cells, in PMA-positive specimens, could be enhanced by exposure to neuraminidase (0.1 unit, 30 min), whereas trypsin or Pronase treatment had no effect on PD41 expression (data not shown). Pretreatment with neuraminidase could not convert a PMA-negative specimen to a PMA-positive specimen.

Reactivity of normal human tissues, fixed or frozen and of non-prostate human carcinoma tissues with MAb PD41 was assessed by immunoperoxidase assay. Results are presented in Tables 3 and 4.

TABLE 3

Reactivity of MAb PD41 to Fixed or Frozen Normal Human Tissues by Indirect Immunoperoxidase Assay

| Tissue type | No. positive/no. tested Frozen | No. positive/no. tested Fixed |
|---|---|---|
| Bladder | 0/3 | 0/3 |
| Blood vessels | 0/3 | 0/4 |
| Brain | 0/6 | 0/5 |
| Breast[a] | 0/5 | 0/3 |
| Bronchus | 0/3 | 0/3 |
| Colon[a] | 0/4 | 0/3 |
| Esophagus | 0/3 | 0/3 |
| Heart | 0/3 | NT[b] |
| Kidney | 0/4 | 0/3 |
| Liver | 0/4 | 0/3 |
| Lung | 0/3 | 0/4 |
| Lymph node | 0/4 | 0/4 |
| Ovary | 0/3 | 0/3 |
| Pancreas | 0/3 | 0/5 |
| Peripheral nerve | 0/3 | 0/1 |
| Salivary gland | NT | 0/2 |
| Skin | 0/2 | 0/3 |
| Spleen | 0/6 | 0/3 |
| Stomach | NT | 0/1 |
| Testicle | 0/3 | 0/4 |
| Uterus | 0/3 | 0/3 |

[a]Epithelial cells negative, an occasional gland or duct showed positive staining of secretory material.
[b]NT, not tested.

TABLE 4

Immunoperoxidase Reactivity of MAb PD41 to Fixed or Frozen Non-Prostate Human Carcinoma[a]

| Tumor type | No. positive/no. tested Frozen | No. positive/no. tested Fixed |
|---|---|---|
| TCC (urinary bladder) | 0/5 | 0/3 |
| Breast | 0/4 | 0/6 |
| Colon | 0/10 | 0/7 |
| Laryngeal | 0/1 | NT[b] |
| Liver | NT | 0/1 |
| Lung (adenocarcinoma) | 0/4 | 0/1 |
| Lung (mesothelioma) | 0/7 | 0/7 |
| Lymphomas | 0/4 | 0/2 |

TABLE 4-continued

Immunoperoxidase Reactivity of MAb PD41 to Fixed or Frozen Non-Prostate Human Carcinoma[a]

| Tumor type | No. positive/no. tested | |
|---|---|---|
| | Frozen | Fixed |
| Ovarian | 0/3 | 0/4 |
| Pancreatic | 0/1 | 0/2 |
| Gastric | 0/2 | 0/5 |
| Carcinoid | NT | 0/1 |

[a]MAb B72.3 or HMFG$_2$ was used as a positive control MAb where appropriate.
[b]NT, not tested.

As demonstrated in Table 3, 21 normal tissue types (represented by 131 specimens) did not react with PD41 MAb. As seen in Table 4, 80 non-prostate carcinoma tissues (12 different types) did not react with the PD41 MAb.

Preliminary experiments demonstrated that the PMA antigen was expressed in 53% of PIN lesions adjacent to PMA-positive staining tumor areas in 73 primary prostate carcinoma tissues tested. Such results indicate that PMA-positive reactivity in areas of PIN could be predictive of disease progression.

Additionally, PMA was found in 79 of 88 (90%) lymph nodes with pathologically diagnosed prostate metastasis. These results also suggest that PMA may be useful in predicting progression of disease.

Reactivity of normal seminal plasma and seminal plasma obtained from patients with a definitive diagnosis of prostate carcinoma was assessed by indirect RIA. Results are presented in Table 5.

TABLE 5

Comparison of Reactivity of Monoclonal Antibodies PD41, anti-PSA, and Anti-PAP in Human Seminal Plasma by Indirect Radioimmunoassay

| | Reactivity[a] | | |
|---|---|---|---|
| Specimen[b] | PD41.84 (IgG1) | anti-PSA (IgG1) | anti-PAP (IgG2a) |
| Normal seminal plasma pool | − | + | + |
| Seminal plasma (carcinoma)[d] | | | |
| 1. WD | + | + | − |
| 2. MD | − | + | + |
| 3. MD | − | + | − |
| 4. MD | − | + | − |
| 5. WD | − | + | + |
| 6. PD | + | + | + |
| 7. MD | + | + | + |
| 8. WD | − | + | + |

[a]Values greater than 3 times the values for the isotype-matched control antibodies were considered to be positive (+). Isotype-matched negative control MAb, either IgG1 or IgG2a.
[b]For all seminal plasma samples tested, a sample dilution of 1:8 was determined to be the optimal concentration.
[c]Seminal plasma samples were obtained from patients with a definitive diagnosis of prostate carcinoma but who had not yet undergone treatment. WD = well-differentiated; MD = moderately differentiated; PD = poorly differentiated.

Table 5 shows that the PMA antigen could be detected in three of eight CaP seminal plasma samples by RIA, although it was not detected in normal seminal plasma. Comparison of MAbs to PSA and PAP (generated in our laboratory) indicated that these antigens were detectable, as expected, in both types of seminal plasma specimens.

Strong PMA reactivity was also observed in immunoblot studies of split ejaculates and prostatic fluids obtained from prostate carcinoma patients. A sample of ejaculate or prostatic fluid was spotted on PVDF membrane, dried, reacted with MAb PD41 and I-125 labeled sheep anti-mouse IgG and exposed to x-ray film. Strong PMA reactivity was seen in both split ejaculate and prostatic fluids.

In similar preliminary immunoblot studies, of urine of prostate carcinoma patients some indication of the presence of PMA in urine has been demonstrated.

4. Characterization of PMA Antigen

Preliminary characterization of the PMA antigen and molecular weight determination of the PD41 reactive bands were obtained by Western blot analysis of normal, benign and prostate carcinoma tissues as well as other normal and non-prostate carcinoma tissues. Results are presented in FIG. 3.

Figure 3A:
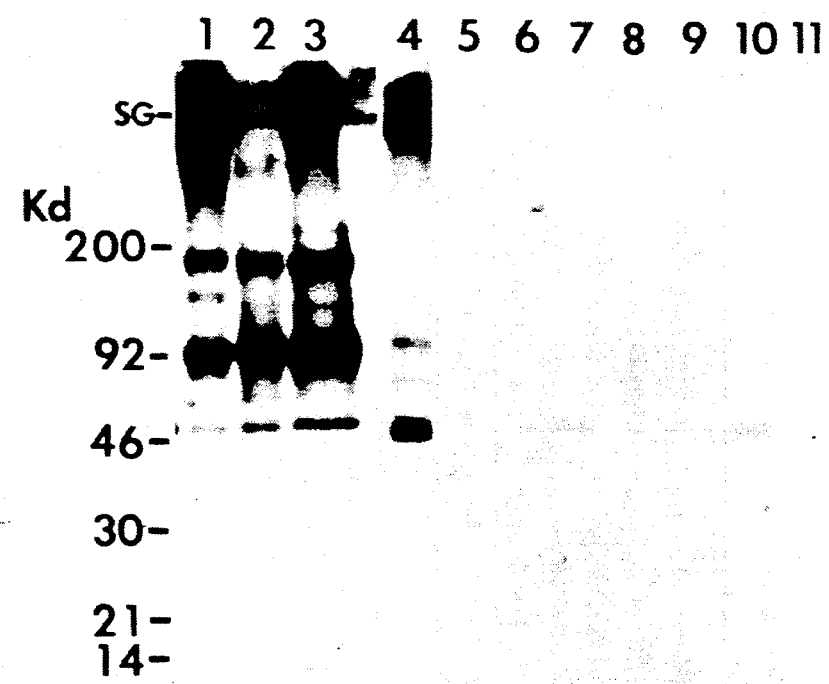

FIG. 3A is a representative immunoblot developed with the PD41 MAb. The most prominent band observed, a large diffuse band ($M_r > 400,000$) is seen in both the CaP tissue extracts (FIG. 3A, Lanes 1 and 3) and CaP seminal plasma (FIG. 3A, Lane 4), although this band was not observed in all CaP tissue extracts FIG. 3A, Lane 2). Two other prominent components reactive with MAb PD41, a $M_r$ 166,000 and a $M_r$ 91,000 band, were usually observed in all the CaP extracts examined. (FIG. 3A, Lanes 1-3), however, occasionally, additional minor bands were observed in some CaP tissues. It also can be noted that the pattern (i.e., number and mobility of bands) reacting with the PD41 MAb, especially the high molecular weight components ($M_4 > 400,000$), differed among individual tumors. However, the absence of MAb PD41 reactive bands in tissue extracts from normal prostate, BPH, breast and colon carcinomas, and normal seminal plasma (FIG. 3 A, Lanes 7 and 8, 9 and 10, 5 and 6) clearly confirmed the restricted distribution of PMA to prostate carcinoma.

Figure 3B:
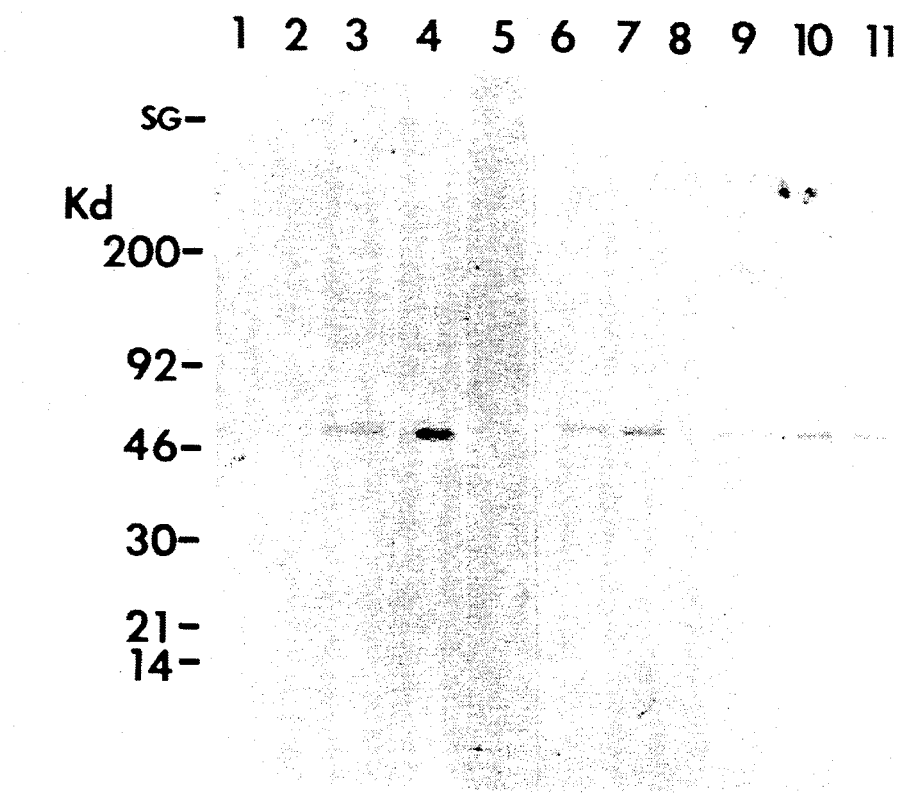

Evidence that the reactivity observed on the PD41 MAb immunoblot was specific was provided by an identical immunoblot stained with an isotype-matched control antibody (FIG. 3B). A non-specific $M_r$ 55,000 band seen on both blots (FIGS. 3A and 3B) was identified as endogenous human IgG heavy chain (data not shown). The control blot showed no other positive bands. All membrane preparations used in this assay, when tested for the presence of residual endogenous protease activity (Endoproteinase Biochemical Test Combination kit; Boehringer Mannheim GmbH, Federal Republic of Germany), were found to be negative (data not shown). This assures that the multiple banding pattern was not the result of enzymatic cleavage during membrane extract preparation.

A series of biochemical assays were conducted to further characterize the PMA antigen having a molecular weight of >400 kd under reducing, conditions. Sensitivity of the PMA antigen to physiochemical and enzymatic treatment was investigated. In view of the relationship between an epitope found in bovine submaxillary mucin (BSM) and another mucin-reactive MAb, i.e., MAb B72.3, Kjeldsen et al., 1988, Cancer Res. 48:2214–2220, B8M was included in the experiments. Results are presented in Table 6.

TABLE 6

Percent Control Binding of PD41 MAb to its Target Antigen Following Enzymatic or Chemical Treatment of the PMA Antigen

| | % Control Binding[a] | |
|---|---|---|
| Treatments of PMA Antigen | CaP | BSM[b] |
| Physical/Chemical: | | |
| Heat (100° C.) | 95 | 98 |

TABLE 6-continued

Percent Control Binding of PD41 MAb to its Target Antigen Following Enzymatic or Chemical Treatment of the PMA Antigen

| | % Control Binding[a] | |
|---|---|---|
| Treatments of PMA Antigen | CaP | BSM[b] |
| Alkali-Borohydride | 10 | 13 |
| pH 4.5 | 139 | 266 |
| pH 11.0 | 77 | 85 |
| Sodium Meta-Peroidate | 2 | 7 |
| Glycosidase Treatments of PMA Antigen: | | |
| Neuraminidase | 145 | 160 |
| Chondroitinase ABC | 100 | 104 |
| Alpha Fucosidase | 103 | 106 |
| N-Glycanase | 104 | 146 |
| Endo-F | 104 | 106 |
| Mixed Glycosidases | 4 | NT |
| O-Glycanase | 9 | 24 |
| Beta-Galactosidase | 30 | 45 |
| Proteolytic Digestion of PMA Antigen: | | |
| Pronase | 20 | 0.2 |
| Protease Type XIV | 7 | N |
| Protease Type XXI | 15 | 8 |
| Protease Type XXVII | 14 | 7 |
| Trypsin | 5 | 4 |
| Alpha Chymotrypsin | 14 | 10 |

[a]Percent control binding of the PD41 antibody to its target antigen (prostate carcinoma tissue membrane extract or bovine submaxillary mucin) was determined by comparing the cpms of the untreated antigen with those obtained after various antigen treatments in a standard solid phase radioimmunoassay. Binding of the antibody to the untreated antigen is considered to be 100%.
[b]Bovine submaxillary mucin.

As shown in Table 6, the PMA antigen is sensitive to treatment with various proteolytic enzymes. Additionally, the PMA antigen is sensitive to agents which affect carbohydrate moieties, including sodium borohydride, sodium meta-periodate, O-glycanase, and beta-galactosidase. Such results indicate that carbohydrate forms an important portion of the PD41 proteinaceous antigen.

Additional experiments were conducted to investigate the carbohydrate moiety of the PMA antigen using standard RIA procedures. (See. e.g., Starling et al., 1982, Cancer Res. 42: 3084–3089; Riott et al. in Immunology, Ch. 25, Section 25.9, St. Louis, Mo., Mosby Co., 1985; Goding in Monoclonal Antibodies: Principles and Practice, 2d ed., pp 75–78, Orlando, Fla., Academic Press, 1986). Results of blocking experiments with MAb PD41 with a variety of carbohydrates and lectins are presented in Tables 7 and 8.

TABLE 7

Carbohydrate Blocking of PD41 MAb Binding to PMA

| Carbohydrate | Percent Control Binding[a] |
|---|---|
| Galactose | 87 |
| Mannose | 79 |
| Maltose | 83 |
| N-Acetyl Galactosamine | 70 |
| N-Acetyl Glucosamine | 94 |
| N-Acetyl-Lactosamine | 81 |
| Sialic Acid | 98 |
| Stachyose | 80 |
| 2-Acetamido-2-Deoxy-3-O-α-Galactopyranosyl Galactopyranose | 93 |
| Raffinose | 70 |

[a]PD41 binding in the absence (100%) and presence of various mono-, di- and polysaccharides was determined by standard radioimmunoassay.

TABLE 8

Lectin Blocking of PD41 MAb Binding to PMA

| Lectin[a] | % Control Binding[b] | Specificity |
|---|---|---|
| PBS | 100 | CONTROL |
| BPA | 95 | D-GalNAc |
| CON A | 112 | alpha man |
| DBA | 95 | alpha GalNAc |
| GS-I | 110 | alpha Gal; GalNAc |
| GS-II | 97 | beta D-GlcNAc |
| LPA | 100 | sialic acid |
| MPA | 115 | alpha Gal |
| PNA | 106 | Gal 1→ 3GalNAc |
| UEA | 98 | Fuc 1→ 2Gal |
| WGA | 108 | GLcNAc, sialic acid |
| S-WGA | 107 | beta 1→ 4-D-GlcNAc |
| SBA | 46 | GalNAc, Gal |

[a]Abbreviations: PBS, phosphate buffered saline; BPA, Bauhimina purpurea agglutinin; Con A, concanavalin A; DBA, Dolichos biflourus agglutinin, GS-I, Griffonia simplicifolia I agglutinin; GS-II, Griffonia simplicifolia II agglutinin; LPA, Limulus polyphemus agglutinin; MPA, Maclura pomifora agglutinin; PNA, Arachis hypogea agglutinin; UEA, Ulex europaeus agglutinin; WGA, Triticum vulgaris agglutinin; S-WGA, succinyl-Triticum vulgaris agglutinin; SBA, Glycine max.
[b]Percent control binding was determined by comparing PD41 binding in the absence (100%) and presence of various lectins using a standard radioimmunoassay procedure.

As demonstrated in Table 7, sialic acid does not inhibit binding of the PD41 MAb to PMA, despite the fact that treatment of the antigen with neuraminidase appears to enhance PD41 MAb binding (Table 6). Thus, sialic acid does not appear to be a component of the antigenic determinant of the PMA antigen, although removal of sialic acid residues may expose more of the PD41 antigenic determinant to the PD41 MAb.

As also demonstrated in Table 7, n-acetyl galactosamine and raffinose both blocked binding of PD41 MAb to the PMA antigen by about 30%.

Results of the lectin binding experiments (Table 8) support the glycoprotein nature of the PMA antigen. Only soy bean agglutinin (SBA), which has specificity for GalNAc, Gal, inhibited binding of the PMA antigen to the PD41 MAb (54%). None of the other eleven lectins tested showed any significant inhibition.

Based on all the above evidence the PMA antigen appears to encompass an O-linked glycoprotein of molecular weight >400 kd with N-acetyl galactosamine as the predominant amino sugar of the antigenic epitope, which is most probably mucin in nature.

A series of competitive binding and reciprocal binding experiments were conducted to determine whether the PMA antigen was related to any previously identified mucin tumor associated marker or to any of the human blood group antigens.

Figure 4:
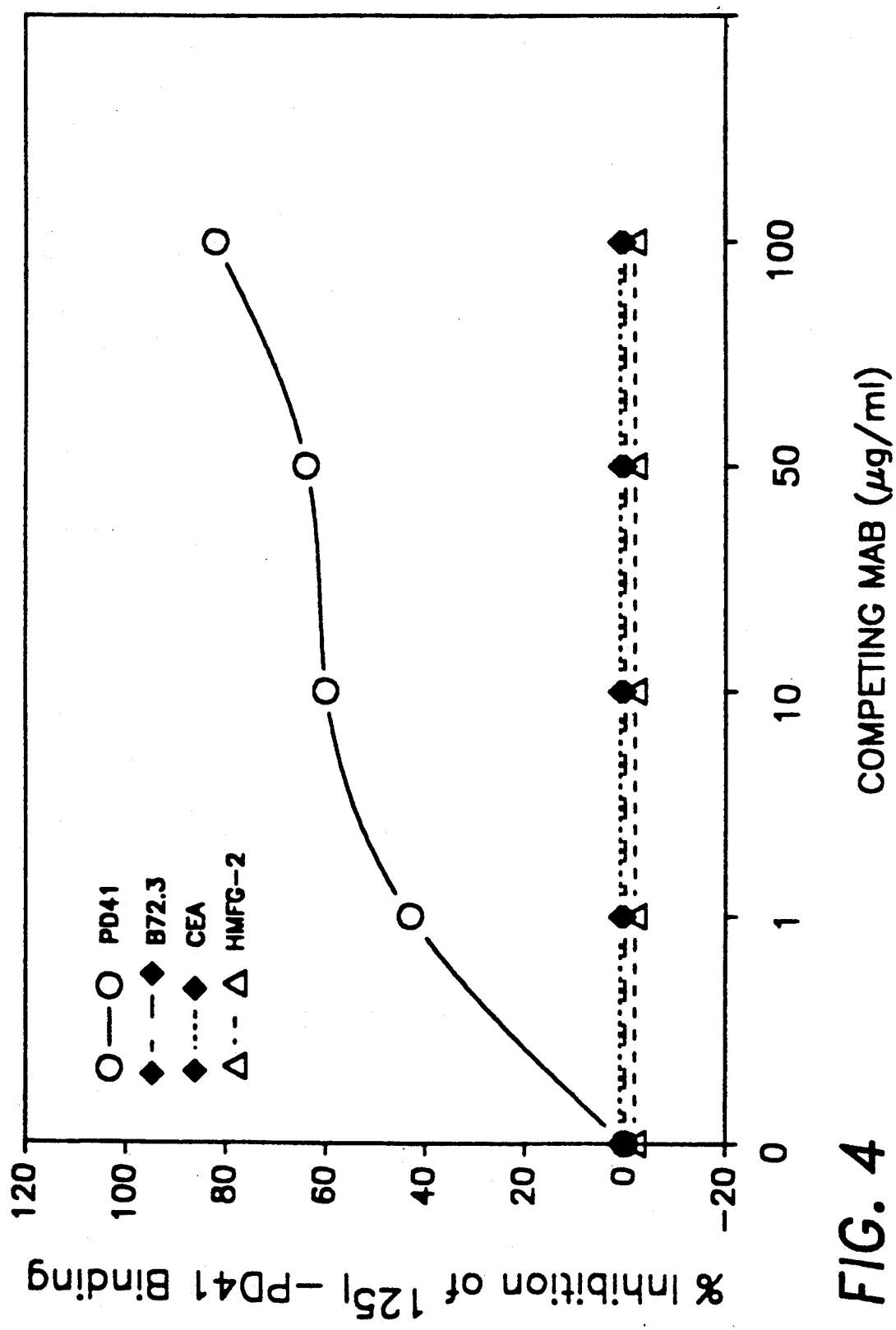
FIG. 4 is a graphic representation of a competitive binding assay of I-125 labeled PD41 MAb against MAbs B72.3, anti-CEA, HMFG-2 and PD41. Each curve represents the mean cpm of triplicate determinations performed in duplicate experiments.

Results of a competitive binding assay (as described above in Section 6.2) presented in FIG. 4, demonstrate that, except for unlabeled PD41, none of the unlabeled antibodies, i.e., B72.3, anti-CEA or HMFG-2, which are known to bind to high molecular weight TAA's, could compete with I-125 labeled MAb PD41 for binding with PMA.

Double determinant immunoradiometric inhibition experiments were conducted as follows. A series of unlabelled MAbs, (listed in Table 9 together with antigens with which such MAbs react) were then added, at a concentration of 100 µg/ml to the target PMA bound to unlabeled "capture" PD41 MAb. Non-saturating amounts of the $^{125}$I-labeled PD41 MAb were then added.

The percent inhibition or blocking of the labelled PD41 MAb to its target antigen was calculated as:

$$100 - \frac{\text{specific binding in presence of blocking antibody}}{\text{specific binding in absence of blocking antibody}} \times 100$$

Figure 5:
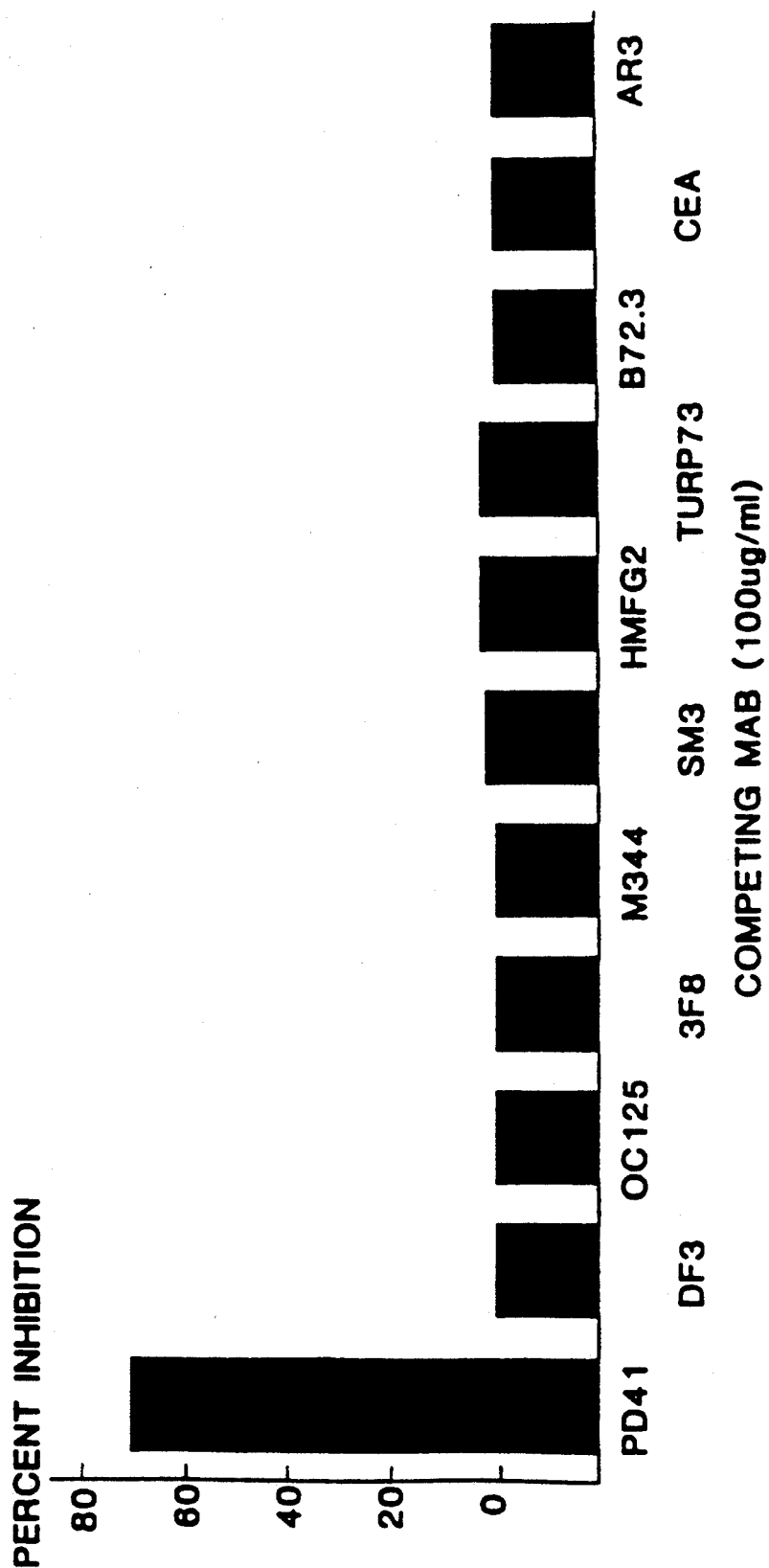
FIG. 5 is graphic representation of a double determinant immunoradiometric assay. See text for details and Table 9 for identification of the tumor-associated MAbs (competing MAbs).

Results are presented in FIG. 5.

TABLE 9

Tumor Associated Antigens and Blood Group Antigens Recognized by Monoclonal Antibodies

| Antigen/Antibody | Type of Cancer or Antigen |
| --- | --- |
| DF3 | Breast |
| OC125 | Ovarian |
| HMFG2 | Breast |
| B72.3 | Breast, ovarian, colon |
| CEA | GI, lung, breast, etc. |
| TURP 73 | Prostate, breast, colon |
| SM3 | Breast (Peptide of HMGF2) |
| AR3 | Pancreas, stomach, colon, uterus, ovarian |
| M344 | Bladder |
| 3F8 | Melanoma, neuroblastoma |
| BG-1* | Precursor (type 1 chain) |
| BG-4* | H-1 |
| BG-5* | Le$^a$ (type 1 chain) |
| BG-6* | Le$^b$ (type 1 chain) |
| BG-7* | X (type 2 chain) |
| GB-8* | Y (type 2 chain) |

*Refers to monoclonal antibodies related to blood group antigens.

As illustrated in FIG. 5, only unlabelled PD41 MAb was able to block (73%) of the binding of the labelled PD41 MAb.

A series of reciprocal blocking experiments using B72.3, CEA, M344, OC125 as well as PD41 as blocking MAbs, were performed as described below: A range of concentrations (0–100 μg/ml) of unlabeled MAbs (blocking) were added to target antigens appropriate for each antibody tested and incubated for 1 h. After washing, non-saturating amounts of I-125 labeled MAb (tracer), as indicated, were added to each well, incubated and the radioactivity remaining in the cells after washing was determined. Results are presented in FIG. 6.

Figure 6:
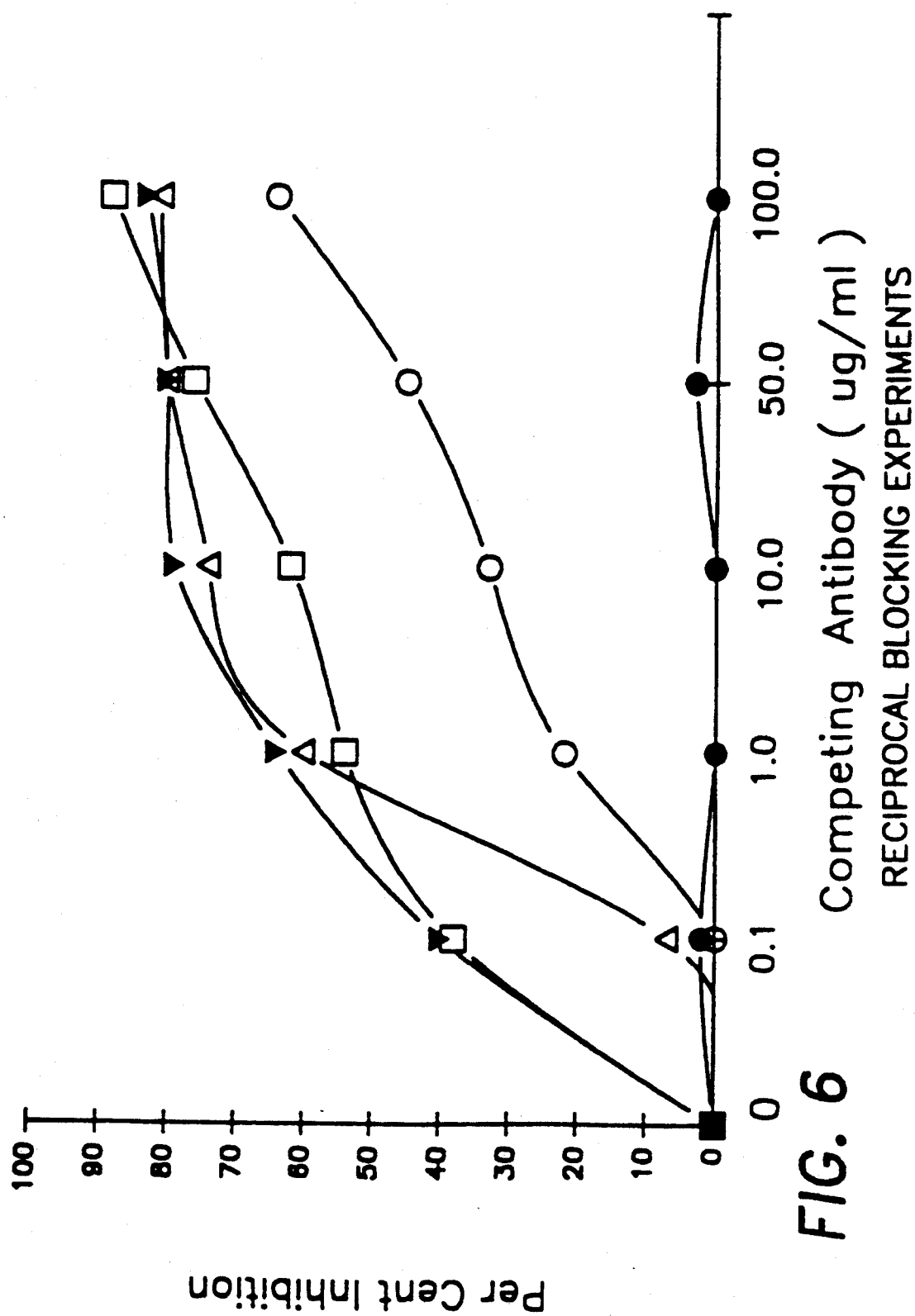
FIG. 6 is a graphic representation of a reciprocal blocking experiment. See text for details and Table 9 for identification of the mucin tumor-associated MAbs. Symbols are as follows: where "Block" represents blocking MAb and "Trace" represents radiolabelled MAb: ○ ○ Block: B72.3, Trace: B72.3; Block: PD41, Trace: B72.3, CEA, M344, OC125; △ △ Block: CEA, Trace: CEA; ☐ ☐ Block: M344, Trace: M344; and ▽ ▽ Block: OC125, Trace OC125.

As shown in FIG. 6, unlabeled PD41 MAb did not block the binding of the selected I-125 labeled MAbs to their respective mucin tumor associated antigen targets. Blocking occurred only with the homologous MAb.

Epitope co-expression was determined using a radioimmunometric assay as described above. In this experiment, the ability of the radiolabelled PD41 MAb to bind target antigen bound by a different capture mucin tumor associated MAb was determined. A series of MAbs which bind to different TAAs were immobilized on the plates to serve as "capture" MAb. Two different prostate carcinoma Surgical specimens previously shown to contain PMA antigen, served as the target antigen to be "captured" by the capture MAbs. These preparations were designated "Antigen 1" and "Antigen 2". Radiolabelled PD41 MAb was then added to determine whether it would bind to whatever antigen bound to the capture MAbs. Results are presented in FIG. 7.

Figure 7:
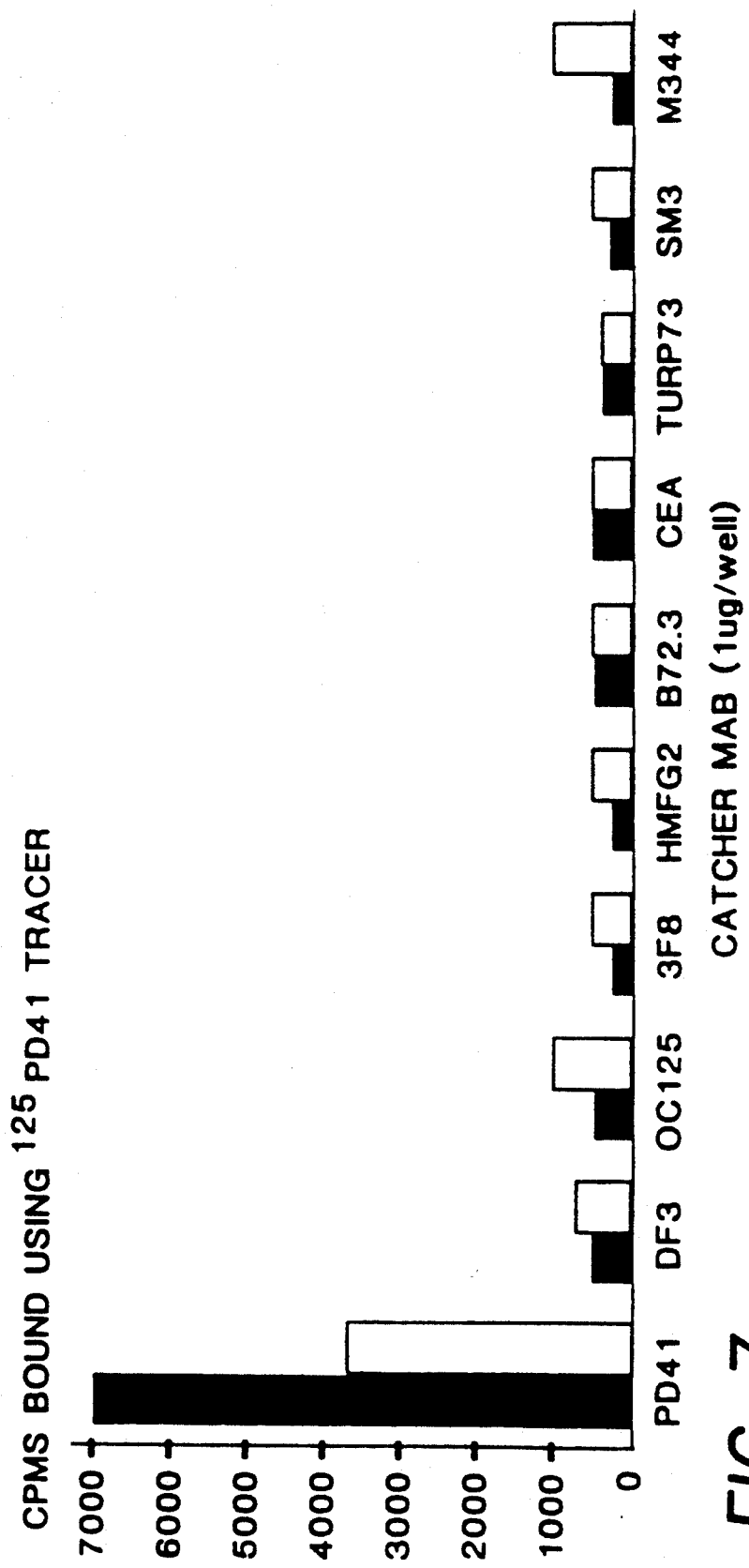
FIG. 7 is a graphic representation of a double determinant immunoradiometric assay to assess epitope coexpression. Symbols indicate: Antigen 1; Antigen 2. See text for details and identification of the tumor-associated MAbs.

As seen in FIG. 7, radiolabelled PD41 MAb showed minimal to no binding to whatever antigen bound to the different tumor mucin "capture" Mabs. Thus, the PMA epitope is not coexpressed on the same glycoproteins recognized by the other tumor Mabs.

In summary, a series of selected Mabs specific for tumor-associated antigen did not block Mab PD41 binding to the PMA target antigen (FIG. 5); and PD41 MAb did not block the tumor-associated MAbs in reciprocal blocking experiments (FIG. 6). MAb PD41 did not bind to target antigens bound to other MAbs which recognize TAA's antigens. Radiolabelled PD41 bound only to the antigen bound to MAb PD41 as "capture" antibody.

Another double determinant immunoradiometric competitive inhibitor experiment was conducted using radiolabelled PD41 MAb against a series of MAbs specific for human blood group antigens listed in Table 9. All of the human blood group MAbs failed to block binding of PD41 MAb to the target PMA antigen (results not shown).

Alteration in glycosylation, particularly incomplete glycosylation, has been observed as a frequent event in tumor cells leading to expression of Tn, sialosyl-Tn and T antigen expression or unmasking of these blood group related antigens in tumor cells. (See, Springer, 1984, Sci 224:1198–1206; Itkowitz et al., 1989, Cancer Res. 49: 197–204; Kjeldsen et al., 1988, Cancer Res. 48:2214–2220). A comparison of the reactivity of PD41 MAb and B72.3 MAb (breast carcinoma) using a standard solid phase RIA was made using bovine and ovine submaxillary mucins and "T" antigen. Results are presented in Table 10.

TABLE 10

PD41 Antigen and its Relationship to TN, SIALOSYL-TN, and T Antigens[a,b]

| Submaxillary Mucins: | Monoclonal Antibody | |
| --- | --- | --- |
| | PD41 | B72.3 |
| Bovine | | |
| (untreated) | 5060 cpm | 6335 cpm |
| (0.1 U neur.) | 7793 cpm | 633 cpm |
| Ovine | | |
| (untreated) | 103 cpm | 6341 cpm |
| (0.1 U neur.) | 125 cpm | 712 cpm |
| "T" Antigen | 201 cpm | 210 cpm |

[a] "T" antigen: Galbl-3GalNAc - R; Tn antigen: GalNAc - R; Sialosyl Tn antigen: Sia 2,6GalNAc - R.
[b] The binding of MAb PD41 and B72.3 to bovine and ovine submaxillary mucin and synthetic "T" antigen linked to human serum albumin were determined using a standard solid phase radioimmunoassay as described in Section 6.2.

As shown in Table 10, PD41 MAb does not react with any of these T,TN and sialosyl-TN antigens.

As can be seen from the data, neither antibody reacts with the "T" antigen. B72.3 reacts with both bovine (with approximately 50% of the carbohydrate chains consisting of sialosyl-Tn) and ovine (90% sialosyl-Tn) submaxillary mucin in the native state, but not after desialylation with neuraminidase, thus indicating B72.3 recognizes the sialosyl-Tn form. PD41 reactivity with bovine submaxillary mucin occurs in the native state and is enhanced following neuraminidase treatment. PD41 does not react with ovine submaxillary mucin in the native state (sialosyl-Tn) or in the neuraminidase treated state (Tn). Immunoperoxidase staining of tissues showed that PMA was expressed by bovine (confirming the above finding) but not by ovine, porcine, monkey or human submaxillary tissues (data not shown).

Reactivity of MAb PD41 with BSM was confirmed by immunoblotting which indicated a similar antigenic molecular weight distribution as that seen for the PMA antigen obtained from prostate carcinoma tissues. Results of biochemical and immunochemical experiments indicate that the antigen detected in BSM had the same or substantially similar biochemical characteristics as the PMA antigen present in extracts of prostate carcinoma tissues or fluids from prostate cancer patients.

Based on the biochemical and immunochemical evidence derived from the above experiments, the PD41 monoclonal antibody reacts with a distinct and novel mucin antigen selectively expressed by human prostate carcinoma cells and by the bovine submaxillary gland, and is not related to any previously described mucin-associated tumor antigen. The PMA antigen, therefore, is a new and unique mucin that has not been previously described.

Deposit of Cell Lines

A cell line, PD41, as described herein has been deposited with the American Type Culture Collection, 12301 Darlawa Drive, Rockville, Md., 20852 USA; and been assigned accession number ATCC No. HB 11094. The invention described and claimed herein is not to be limited in scope by the cell lines deposited since the deposited embodiment is intended as an illustration of one aspect of the invention and any equivalent cell lines which produce functionally equivalent monoclonal antibodies are within the scope of this invention. Indeed, various modifications of the invention in addition to those shown and described herein will become apparent to those skilled in the art from the foregoing description. Such modifications are also intended to fall within the scope of the appended claims.

It is apparent that many modifications and variations of this invention as set forth above may be made without departing from the spirit and scope thereof. The specific embodiments described are given by way of example only and the invention is limited only by the terms of the appended claims.

A number of references are cited in the present specification, the entire disclosure of each of which is incorporated by reference herein, in its entirety.

I claim:

1. Hybridoma cell line having the characteristics of PD41 having ATCC Accession No. HB 11094.

2. A monoclonal antibody, or binding fragment thereof, produced by the cell line according to claim 1.

3. A hybridoma cell line having all identifiable characteristics of the hybridoma having accession No. HB 11094 that produces the binding of the monoclonal antibody of claim 2 to a prostate mucin antigen which is expressed in human prostatic carcinoma but is not expressed in human prostatic hyperplasia or normal human prostatic tissues.

4. A monoclonal antibody, or binding fragment thereof, produced by the cell line according to claim 3.

* * * * *